(12) United States Patent
Matsushige et al.

(10) Patent No.: US 8,513,327 B2
(45) Date of Patent: *Aug. 20, 2013

(54) ADHESIVE COMPOSITION FOR DENTAL USE

(75) Inventors: Koji Matsushige, Tsukuba (JP); Takeshi Suzuki, Tsukuba (JP); Shizuka Shimizu, Sakuragawa (JP); Ayumi Dodomi, Tsukuba (JP)

(73) Assignee: Tokuyama Dental Corporation, Taito-Ku, Tokyo (JP)

( * ) Notice: Subject to any disclaimer, the term of this patent is extended or adjusted under 35 U.S.C. 154(b) by 361 days.

This patent is subject to a terminal disclaimer.

(21) Appl. No.: 12/526,070

(22) PCT Filed: Nov. 8, 2007

(86) PCT No.: PCT/JP2007/072145
§ 371 (c)(1),
(2), (4) Date: Aug. 6, 2009

(87) PCT Pub. No.: WO2008/102489
PCT Pub. Date: Aug. 28, 2008

(65) Prior Publication Data
US 2010/0317762 A1    Dec. 16, 2010

(30) Foreign Application Priority Data

Feb. 19, 2007   (JP) ................................ 2007-038059
Feb. 20, 2007   (JP) ................................ 2007-040031

(51) Int. Cl.
*A61K 6/083*    (2006.01)
*A61C 5/00*     (2006.01)

(52) U.S. Cl.
USPC ..................... 523/118; 433/228.1; 106/35

(58) Field of Classification Search
USPC ..................... 523/118; 433/228.1; 106/35
See application file for complete search history.

(56) References Cited

U.S. PATENT DOCUMENTS

| 4,259,117 | A | | 3/1981 | Yamauchi et al. | |
|---|---|---|---|---|---|
| 5,883,153 | A | * | 3/1999 | Roberts et al. | 523/116 |
| 6,191,190 | B1 | * | 2/2001 | Blackwell et al. | 523/115 |
| 6,217,644 | B1 | | 4/2001 | Matsunae et al. | |
| 6,512,068 | B1 | * | 1/2003 | Nakatsuka | 526/277 |
| 6,583,197 | B1 | | 6/2003 | Wada et al. | |
| 7,767,731 | B2 | * | 8/2010 | Chen et al. | 523/118 |
| 2004/0254261 | A1 | | 12/2004 | Kojima et al. | |
| 2007/0293599 | A1 | * | 12/2007 | Ueyama et al. | 523/120 |
| 2009/0076189 | A1 | * | 3/2009 | Matsushige et al. | 523/120 |
| 2010/0292360 | A1 | * | 11/2010 | Jia et al. | 522/109 |

FOREIGN PATENT DOCUMENTS

| JP | 52-113089 A | 9/1977 |
|---|---|---|
| JP | 53-113843 A | 10/1978 |
| JP | 58-21687 A | 2/1983 |
| JP | 7-82115 A | 3/1995 |
| JP | 9-263604 A | 10/1997 |
| JP | 10-236912 A | 9/1998 |
| JP | 11-130465 A | 5/1999 |
| JP | 2000-86421 A | 3/2000 |
| JP | 2000-159621 A | 6/2000 |
| JP | 2001-72523 A | 3/2001 |
| JP | 2004-352698 A | 12/2004 |

* cited by examiner

*Primary Examiner* — Tae H Yoon
(74) *Attorney, Agent, or Firm* — Buchanan Ingersoll & Rooney PC

(57) ABSTRACT

An adhesive composition for dental use exhibiting acidic property, including a mixture of a polymerizable monomer component (A) containing a phosphoric acid-type polymerizable monomer having an acidic group derived from phosphoric acid, and a multivalent metal ion-releasing component (B), wherein the multivalent metal ion-releasing component (B) is capable of releasing at least earth metal ions, and in the composition, earth metal ions stemming from the component (B) are present together with the phosphoric acid-type polymerizable monomer in such an amount that a total valency ratio ($R_E$) defined by the following formula (1) is in a range of 0.2 to 3.0. The adhesive composition is capable of strongly adhering and fixing a composite resin or a prosthetic material to a tooth for extended periods of time maintaining stability.

$$R_E = TV_E/TV_A \quad (1)$$

wherein $TV_E$ is a total valency of the earth metal ions contained in said composition, and
$TV_A$ is a total valency of the acidic groups of the phosphoric acid-type polymerizable monomer contained in said composition.

8 Claims, No Drawings

ADHESIVE COMPOSITION FOR DENTAL USE

TECHNICAL FIELD

This invention relates to a dental adhesive composition for adhering a dental restorative comprising a metal, an organic high molecular material, ceramics or a composite material thereof to a tooth in the field of dental therapy.

BACKGROUND ART

When a tooth is damaged due to decaying and when a cavity caused by the damage is still relatively small, the tooth is, in many cases, directly restored by using a composite resin from the standpoint of aesthetic appearance, simplicity and quickness of operation. When the cavity caused by the damage is relatively large, on the other hand, the cavity is restored by using a prosthetic material prepared by using a metal, ceramics or a cured resin material.

The dental restorative such as a composite resin or a prosthetic material has no adhesiveness to the tooth. Therefore, the restorative is adhered to the tooth by using an adhesive which comprises a polymerizable composition. The polymerizable composition used as the adhesive, usually, contains a methacrylate-type monomer as the polymerizable monomer which is a chief component but its adhesive force to the tooth is not sufficient. For example, when the polymerizable composition is used for adhering the composite resin to the tooth, the adhesive strength that is obtained is not, in many cases, large enough to overcome the internal stress (tensile stress occurring in the interface between the tooth and the composite resin) that generates when the composite resin cures. In many cases, further, the adhesive strength is not large enough to withstand the force produced by occlusion.

In order to improve the adhesive strength of the adhesive, therefore, at the time of using the adhesive, the tooth surface is pre-treated, such as:

(a) a hard tooth (enamel comprising chiefly hydroxyapatite) is etched, and
(b) an adhesiveness-improving component called primer is penetrated into the tooth.

Here, an aqueous solution of acid for demineralizing the tooth surface is usually used as a pre-treating agent for etching. Namely, an aqueous solution of phosphoric acid, citric acid or maleic acid is used.

After the etching (demineralizing), further, a dentin is exposed on the surface of the tooth, the dentin comprising an enamel or spongy collagen fiber that is coarsely granulated due to demineralizing with the acid aqueous solution. To maintain a sufficiently large adhesive strength, however, the adhesive component must penetrate through the tooth surface and curing must be performed in this condition. As the primer for the penetration treatment, therefore, there has been used a polymerizable monomer composition which contains an organic solvent or a hydrophilic monomer having good affinity to the tooth, such as hydroxyethyl methacrylate (HEMA). Though the primer by itself does not usually contain any polymerization initiator, the polymerizable monomer in the primer is polymerized and cured by the action of radicals formed by the adhesive at the time when the adhesive for the composite resin applied thereon undergoes the photo-curing reaction.

While the pre-treatment is conducted as described above, there have been developed various dental adhesive compositions containing a polymerizable monomer having adhesiveness to the tooth in order to attain higher adhesive strength and to reduce complexity of pre-treating operation.

For example, patent documents 1 and 2 propose dental adhesive compositions containing an acidic group-containing polymerizable monomer as at least part of the polymerizable monomer component. These adhesive compositions exhibit higher adhesive strengths since the acidic group-containing polymerizable monomer having an acidic group such as phosphoric acid group or carboxylic acid group in the molecules thereof has a high affinity to the tooth (hydroxyapatite or collagen).

Further, patent documents 3 to 6 propose adhesive compositions in which an acidic group-containing polymerizable monomer is present together with water. These adhesive compositions exhibit both the demineralizing function due to the acid aqueous solution based on the action of the acidic group and the primer penetration accelerating function, and eliminate the need of separately applying a pre-treating agent. Namely, these adhesive compositions can be used upon being applied only once, and can be advantageously used as adhesives (one-step type adhesives) featuring excellent operability. Further, by also utilizing their etching property and penetrating property, the adhesive compositions containing the acidic group-containing polymerizable monomer can be used as self-etching primers having the above two functions (e.g., see patent document 8 and patent document 9).

A patent document 10 reports that the adhesive strength can be further improved if a polymerizable monomer having a phosphoric acid group as an acidic group is used in the form of a calcium salt.

Among the above various prior arts, patent documents 4 to 7 propose adhesives and self-etching primers containing an acidic group-containing polymerizable monomer and water, which are blended with an earth metal ion-eluting fillers. Here, the earth metal ion-eluting filler is a filler such as a fluoroaluminosilicate glass, that elutes out metal ions in an acidic solution. The metal ions eluted out therefrom are the ions of alkaline earth metals and aluminum. The adhesive compositions containing the filler that elutes out earth metal ions are supposed to further improve the adhesive strength presumably due to that the polymerizable monomer component containing the acidic group-containing polymerizable monomer is cured by polymerization and, besides, multivalent metal ions eluted out from the earth metal ion-eluting filler undergo the ionic crosslinking with the acidic groups of the acidic group-containing polymerizable monomer causing an increase in the strength of the obtained cured body.

Patent document 1: JP-A-52-113089
Patent document 2: JP-A-58-21687
Patent document 3: JP-A-2004-352698
Patent document 4: JP-A-9-263604
Patent document 5: JP-A-10-236912
Patent document 6: JP-A-2001-72523
Patent document 7: JP-A-2000-86421
Patent document 8: JP-A-7-82115
Patent document 9: JP-A-2000-159621
Patent document 10: JP-A-53-113843

DISCLOSURE OF THE INVENTION

The adhesive compositions such as the adhesives and primers containing the acidic group-containing polymerizable monomer make it possible to obtain higher adhesive strengths than those without containing the monomer and, further, have the demineralizing function. Therefore, no etching treatment needs to be executed, and the adhesion operation can be simplified. However, since a very strong adhesive strength is required for adhering the dental restorative to the tooth, the adhesive strengths obtained above are not still sufficient, and still higher adhesiveness is desired maintaining stability.

Further, among the above known adhesive compositions, those blended with a calcium salt of the phosphoric acid-containing polymerizable monomer or the earth metal ion-eluting filler exhibit adhesive strengths of considerably high levels which, however, are not still satisfactory.

The present inventors have forwarded extensive experiment and study concerning the adhesive compositions blended with the acidic group-containing polymerizable monomer and the earth metal ion-eluting filler, and have come to presume that the effect for improving the adhesive strength has not been exhibited to a sufficient degree because of the following reasons.

As the polymerization initiators to be added to the adhesives according to the above prior arts, for example, there are used such compounds as allyl borate compounds that work as radical initiators upon reacting with an acid. By taking the preservation stability into consideration, the adhesive composition containing the polymerization initiator is preserved being separated into a component that contains the acidic group-containing polymerizable monomer and water, and a component that contains the polymerization initiator that generates radicals upon reacting with an acid (acidic group-containing polymerizable monomer) and being contained in separate packages as disclosed in the patent document 5. In the preservation of this form, it is a common practice to preserve the earth metal ion-eluting filler and the acidic group-containing polymerizable monomer in separate packages, i.e., containing the earth metal ion-eluting filler in the package which is filled with the component containing the polymerization initiator. As also disclosed in the patent document 6, this is to avoid an increase in the viscosity of the composition with the passage of time stemming from the ionic bonds of the multivalent metal ions eluting from the earth metal ion-eluting filler with the acidic group-containing polymerizable monomer.

Here, when the constituent components are preserved being separated into two packages as described above, the components filled in the two packages are mixed together to prepare a mixed liquid which is then applied to the tooth surface consuming a working time of as very short as several minutes. Therefore, the earth metal ion-eluting filler which does not quickly dissolve in the acid aqueous solution permits the multivalent metal ions to elute out in only very small amounts in this short period of time. Namely, the multivalent metal ions eluted out from the earth metal ion-eluting filler do not effectively act to improve the adhesive force (formation of ionic crosslinking by the acidic group and multivalent metal ions), and the effect is not sufficiently exhibited for improving the adhesive force.

According to the above patent document 4, for example, the constituent components are prepared as one liquid and are readily subjected to the adhesion testing to evaluate the adhesive force of the composition. However, the time for dissolving the earth metal ion-eluting filler is so short that the ionic crosslinking is not sufficiently formed at the time of curing. Namely, the adhesive force is improved to some degree but cannot be improved to a striking degree.

Further, when it is attempted to develop the ionic crosslinking to a sufficient degree to obtain a high adhesive strength with the adhesive composition blended with the earth metal ion-eluting filler, a very important role is also played by the kinds and amounts of metal ions eluted out from the earth metal ion-eluting filler. For example, if the eluted metal ions are chiefly monovalent metal ions or divalent metal ions such as calcium ions, the adhesiveness cannot be sufficiently improved. Further, if the metal ions are eluted out in too large amounts, the water resisting property of the cured body greatly decreases. That is, even if a considerably large adhesive force is obtained right after the curing, the adhesive force gradually decreases after having stayed in the restored portion of the tooth for extended periods of time. As a result, the dental restorative tends to peel off easily.

It is, therefore, an object of the present invention to provide an adhesive composition for dental use containing an acidic group-containing polymerizable monomer featuring further improved adhesiveness and durability, and is capable of stably maintaining the adhesion between the composite resin or the prosthetic material and the tooth maintaining strength for extended periods of time.

The present inventors have discovered the fact that the above problems can be solved if a dental adhesive composition contains, particularly, a polymerizable monomer having an acidic group derived from phosphoric acid among the polymerizable monomers containing various acidic groups and if earth metal ions are made present in a particular amount in the solution thereof, and have completed the invention.

According to the present invention, there is provided an adhesive composition for dental use exhibiting acidic property, which includes a mixture of a polymerizable monomer component (A) containing a phosphoric acid-type polymerizable monomer having an acidic group derived from phosphoric acid, and a multivalent metal ion-releasing component (B); wherein said multivalent metal ion-releasing component (B) is capable of releasing at least earth metal ions; and earth metal ions stemming from said component (B) are present together with the phosphoric acid-type polymerizable monomer in such an amount that a total valency ratio ($R_E$) defined by the following formula (1) is in a range of 0.2 to 3.0 in said composition;

$$R_E = TV_E / TV_A \qquad (1)$$

wherein $TV_E$ is a total valency of the earth metal ions contained in said composition, and $TV_A$ is a total valency of the acidic groups of the phosphoric acid-type polymerizable monomer contained in said composition.

In the present invention, the earth metals are the metals belonging to the Group 3 and the Group 13 of periodic table.

In the adhesive composition for dental use of the present invention, it is desired that:

(1) the earth metal is aluminum and/or lanthanum;
(2) the component (B) is an earth metal ion-eluting filler;
(3) the component (B) is a carbonate of an acid and an earth metal, a lower alkoxide of an earth metal having not more than 4 carbon atoms, or a hydroxide;
(4) the polymerizable monomer component (A) contains not less than 5 mass % of the phosphoric acid-type polymerizable monomer;
(5) the phosphoric acid-type polymerizable monomer is a compound having a dihydrogenphosphoric monoester group and/or a hydrogenphosphoric diester group;
(6) water (C) is, further, contained;
(7) fumed silica (D) is, further, contained; and
(8) a polymerization initiator (E) is, further, contained.

In the formula representing the total valency ratio ($R_E$), the total valency ($TV_A$) of acidic groups of the phosphoric acid-type polymerizable monomer (phosphoric acid-type monomer) contained in the adhesive composition is calculated according to the following formula (1a), $$TV_A = \Sigma P_k \times A_k \qquad (1a)$$

wherein k is 1, 2, 3, - - -, n, and n is a number of kinds of phosphoric acid-type monomers contained in the composition, $P_k$ is a mol number of the phosphoric acid-type monomers contained in the composition, and $A_k$ is a valency of the acidic group possessed by the phosphoric acid-type monomers.

For example, if the phosphoric acid-type monomer is a dihydrogenphosphoric mono(2-methacryloxyethyl)ester, the valency of the acidic group is divalent. If the phosphoric acid-type monomer is a hydrogenphosphoric di(2-methacryloxyethyl)ester, the valency of the acidic group is monovalent. If the composition contains one kind of phosphoric acid-type monomer (e.g., only a phosphoric acid-type monomer containing monohydric acidic group or divalent acidic group), the valency calculated for the phosphoric acid-type monomer according to the above formula becomes the total valency ($TV_A$). If the composition contains a plurality of kinds of phosphoric acid-type monomers, the valencies are calculated for the phosphoric acid-type monomers and the sum thereof becomes the total valency ($TV_A$).

On the other hand, the total valency ($TV_E$) of the earth metal ions contained in the composition is calculated according to the following formula (1b), $$TV_E = 3M_E \qquad (1b)$$

wherein $M_E$ is a mol number of the earth metal ions contained in the composition, since the valency of the earth metal ions is 3.

The kind and amount of the earth metal ions present in the dental adhesive composition of the present invention can be found by taking measurements by using an inductively coupled plasma (ICP) emission analyzer after the solid components have been removed. For example, the adhesive composition is diluted with a water-soluble organic solvent down to a concentration of 1 mass %, and the obtained diluted solution is filtered by using a syringe filter to remove solid components. Thereafter, the ion species and the ion concentration of the obtained filtrate are measured by using the ICP emission analyzer, and the kind and amount of the earth metal ions in the adhesive composition are calculated.

The kinds and amounts of metal ions other than the earth metal ions can also be measured by a similar method.

The kind and amount of the acidic group possessed by the phosphoric acid-type polymerizable monomer (phosphoric acid-type monomer) in the dental adhesive composition can be found by isolating the phosphoric acid-type monomer from the composition by using a high-performance liquid chromatography for separation, measuring the molecular amount thereof from the mass analysis of the isolated phosphoric acid-type monomer and, further, the structure can be determined by the nuclear magnetic resonance spectrum (NMR) to identify the acidic group and to calculate the amount thereof.

For example, upon measuring the NMR of $^{31}P$, the kind of acidic group derived from the phosphoric acid can be identified relying on the chemical shift values. That is, a known compound having an acidic group derived from the phosphoric acid is used as a standard substance and is measured for its $^{31}P$-NMR under the same conditions (diluted solvent, concentration, temperature), which is then compared with the $^{31}P$-NMR measured for the adhesive composition to determine the chemical shift values thereof. A dimethylphosphinic acid is used as a standard substance of the phosphoric acid-type monomer having a phosphinic acid group as the acidic group, a methylphosphonic acid is used as a standard substance of the phosphoric acid-type monomer having a phosphonic acid group, a hydrogenmethylphosphonic monoethyl ester is used as a standard substance of the phosphoric acid-type monomer having a hydrogenphosphonic monoester group, a dihydrogenphosphoric monomethyl ester is used as a standard substance of the phosphoric acid-type monomer having a dihydrogenphosphoric monoester group, and a hydrogenphosphoric dimethyl ester is used as a standard substance of the phosphoric acid-type monomer having a hydrogenphosphoric diester group.

The amount of the phosphoric acid-type monomer in the composition can be found by preparing a calibration curve with respect to the standard substance from the phosphoric acid-type monomer isolated by using the high-performance liquid chromatography for separation, and by taking a measurement by using the high-performance liquid chromatography while adding an internal standard substance to part of the filtrate.

The dental adhesive composition of the present invention can be preferably used as a dental adhesive or a dental pretreating agent.

According to the present invention, further, there is provided a method of producing an adhesive composition for dental use comprising following steps of;

homogeneously mixing:

(A) a polymerizable monomer component containing a phosphoric acid-type polymerizable monomer having an acidic group derived from phosphoric acid;

(B) a multivalent metal ion-releasing component capable of releasing at least earth metal ions; and (C) water; and aging the obtained mixture so that the amount of the earth metal ions released from said component (B) into the obtained mixture maintains a total valency ratio ($R_E$) defined by the following formula (1) to lie in a range of 0.2 to 3.0;

$$R_E = TV_E / TV_A \qquad (1)$$

wherein $TV_E$ is a total valency of the earth metal ions contained in said mixture, and $TV_A$ is a total valency of the acidic groups of the phosphoric acid-type polymerizable monomer contained in said mixture.

In the dental adhesive composition of the present invention, among various multivalent metal ions, the earth metal ions are present together with the phosphoric acid-type polymerizable monomer (phosphoric acid-type monomer) in such an amount that the total valency ratio ($R_E$) is in a range of 0.2 to 3.0. It is, therefore, considered that the earth metal ions undergo ionic bond with the acidic groups possessed by the phosphoric acid-type monomer forming ionic crosslinking in sufficient amounts at the time of curing. Due to the synergistic action of the ionic crosslinking and the curing of the polymerizable monomer, therefore, a very high adhesive strength is exhibited to the tooth (either dentin or enamel). When used for adhering a dental restorative to the tooth, therefore, the adhesive exhibits an adhesive strength large enough to withstand a tensile stress that occurs in the interface between the restorative such as composite resin and the tooth. When used for fixing the dental restorative to a predetermined portion, too, the adhesive exhibits an adhesive strength large enough to withstand the force exerted by occlusion.

Though the reason has not been clarified yet why a high adhesive strength is obtained if in the present invention a particular amount of earth metal ions are made present together with the phosphoric acid-type monomer, the inventors postulate as described below.

That is, if metal ions are made present in a system which contains the phosphoric acid-type monomer, the acidic groups of the phosphoric acid-type monomer undergo the ionic bonding with the metal ions, and ionic crosslinking occurs if the metal ions are multivalent. The ionic crosslinking developed and formed to a sufficient degree by the polymerization reaction of the polymerizable monomer synergistically acts on increasing the adhesive force that is produced by curing by polymerization. In the present invention, among various kinds of multivalent ions, if earth metal ions (having a valency of 3) are made present, it is considered that the ionic crosslinking develops to a sufficient degree and a high adhesive strength is obtained. With divalent metal ions such as calcium ions, for example, the valency is small and the ionic crosslinking cannot be sufficiently developed. Among the multivalent metal ions having valencies of 3 or more, the earth metal ions, in particular, undergo ionic crosslinking with acidic groups derived from phosphoric acid. Upon making earth metal ions present together with the phosphoric acid-type monomer, therefore, the ionic crosslinking develops to a sufficient degree and it is considered that a high adhesive strength is exhibited.

It is, further, necessary that the amount of the earth metal ions present together with the phosphoric acid-type monomer is such that the total valency ratio ($R_E$) represented by the above formula lies within a predetermined range. That is, part of the earth metal ions present in the composition forms ionic crosslinking with the phosphoric acid-type monomer but not the whole amount of the earth metal ions forms the ionic crosslinking. In order to form the ionic crosslinking to a sufficient degree, it is necessary that the earth metal ions are present maintaining a constant balance relative to the acidic groups possessed by the phosphoric acid-type monomer. For this purpose according to the present invention, the total valency ratio ($R_E$) is set to lie in a predetermined range (0.2 to 3.0). For example, if the amount of the earth metal ions that are made present is small as compared to the phosphoric acid-type monomer and the total valency ratio ($R_E$) is smaller than the above range, the ionic crosslinking does not develop to a sufficient degree, and a desired high adhesive strength is not obtained. Further, if the amount of the earth metal ions is large as compared to the phosphoric acid-type monomer and the total valency ratio ($R_E$) is larger than the above range, the amount of the acidic groups is small and the ionic crosslinking does not develop to a sufficient degree and, besides, gelling easily occurs, causing a decrease in the demineralizing action of the phosphoric acid-type monomer. Therefore, a high adhesive strength is not obtained, either. Or, even if a high adhesive strength is obtained, the cured body lacks resistance against the water. Accordingly, the adhesive strength decreases in relatively short periods of time, durability of adhesion is not satisfactory, and the adhesive is no longer suited for use in the dental field.

According to the present invention as described above, the amount of the earth metal ions must be so adjusted with respect to the phosphoric acid-type monomer that the total valency ratio ($R_E$) lies in the range of 0.2 to 3.0. The total valency ratio ($R_E$) is adjusted to lie in a range of, desirably, 0.3 to 0.9 and, most desirably, 0.4 to 0.7.

Further, the dental adhesive composition of the present invention exhibits acidic property and, therefore, also possesses tooth demineralizing ability making it possible to realize a high adhesive strength without effecting the etching operation.

The dental adhesive composition of the present invention not only exhibits a high adhesive strength but also features excellent resistance against water. Therefore, even when held in the oral cavity where water is present for extended periods of time, the dental adhesive composition of the present invention exhibits a high adhesive strength maintaining stability. Therefore, the dental adhesive composition of the present invention is effective as an adhesive being capable of adhering a dental restorative such as a composite resin or a prosthetic material to the tooth and is also effective as a pretreating material to be applied to the tooth surface prior to using the adhesive.

BEST MODE FOR CARRYING OUT THE INVENTION

The dental adhesive composition of the present invention exhibits acidic property and is obtained by mixing a polymerizable monomer component (A) and a multivalent metal ion-releasing component (B), and usually contains water (C) for releasing metal ions from the component (B) and is, further, blended with fumed silica (D) and a polymerization initiator (E) as required. Further, the composition contains an acidic group-containing polymerizable monomer as the polymerizable monomer component (B) and, therefore, exhibits acidic property. The acidity, however, decreases depending upon the amount of metal ions released from the component (B). In such a case, therefore, the acidity is adjusted by adding an acidic substance for adjusting pH. The composition may, further, be blended with various blending agents that have been known in the dental field.

<Polymerizable Monomer Components (A)>

In the present invention, the polymerizable monomer component (A) (hereinafter simply called "monomer component") is cured by polymerization to impart adhesiveness to the composite resin and various prosthetic materials and must contain a phosphoric acid-type polymerizable monomer (A1) for forming ionic crosslinking with the earth metal ions released from the component (B) that will be described later.

The phosphoric acid-type polymerizable monomer (A1) (hereinafter called phosphoric acid-type monomer) is a compound which has in the molecules thereof a polymerizable unsaturated group and an acidic group derived from phosphoric acid.

As the polymerizable unsaturated group, there can be exemplified acryloyl group, methacryloyl group, acrylamide group, methacrylamide group, vinyl group, allyl group, ethynyl group and styryl group. From the standpoint of curing rate, in particular, it is desired to use acryloyl group, methacryloyl group, acrylamide group or methacrylamide group. Most desirably, acryloyl group or methacryloyl group is used.

Further, the acidic group derived from phosphoric acid has a structure represented by >P(=O)OH. Concrete examples include phosphinic acid group, phosphonic acid group, hydrogenphosphonic monoester group, dihydrogenphosphoric monoester group and hydrogenphosphoric diester group. From the standpoint of permeability into the tooth, among them, phosphoric ester groups are desired, such as;

dihydrogenphosphoric monoester group [—O—P(=O)(OH)$_2$] and hydrogenphosphoric diester group [(—O—)$_2$ P(=O)OH].

The acidic group derived from phosphoric acid not only has a high demineralizing action for the tooth but also exhibits an essentially high bonding force to the composite resin and the tooth, further enabling ionic crosslinking to be excellently formed with the earth metal ions as will be described later making it possible to obtain a particularly high adhesive strength.

The following compounds are concrete examples of the phosphoric acid-type monomer containing the phosphoric acid ester-type group.

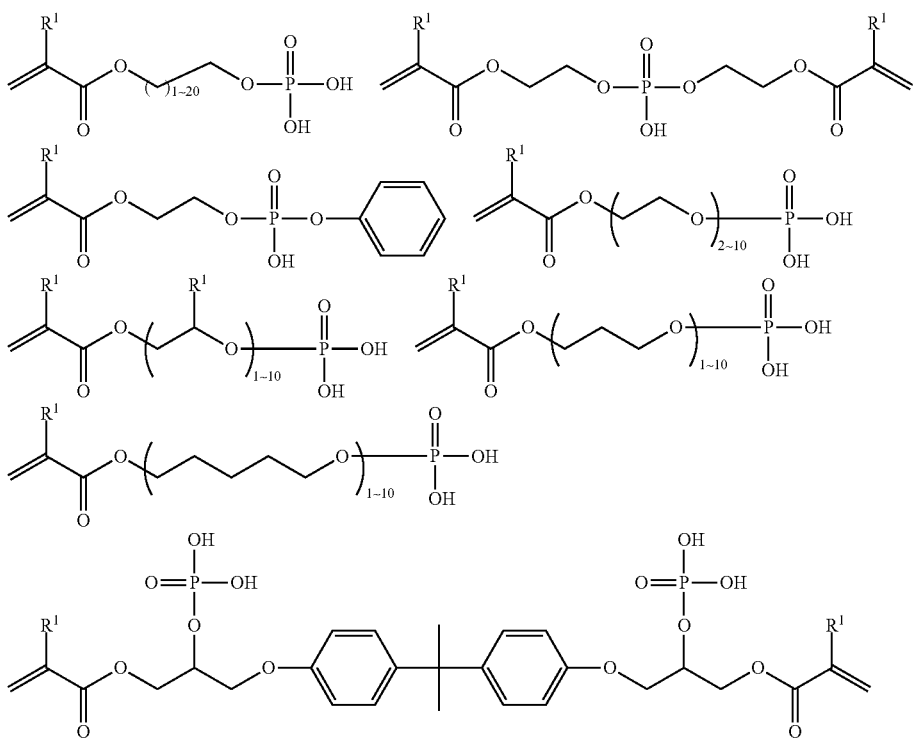

wherein $R^1$ is a hydrogen atom or a methyl group.

The above phosphoric acid-type monomers (A1) may be used in a single kind or in two or more kinds in combination.

The following compounds can be preferably used as the phosphoric acid-type monomer (A1) in addition to the above compounds.

Phosphoric acid-type monomers having a phosphinic acid group;
bis(2-methacryloxy)phosphonic acid,
bis(methacryloxypropyl)phosphinic acid,
bis(methacyloxybutyl)phosphinic acid.
Phosphoric acid-type monomers having a phosphonic acid group;
3-methacryloxypropylphosphonic acid,
2-methacryloxyethoxycarbonylmethylphosphonic acid,
4-methacryloxybutoxycarbonylmethylphosphonic acid,
6-methacryloxyhexyloxycarbonylmethylphosphonic acid,
2-(2-ethoxycarbonylallyloxy)ethylphosphonic acid.
Phosphoric acid-type monomers having a hydrogenphosphonic monoester group;
2-methacryloxyethylphosphonic mono(methacryloxyethyl) ester,
2-methacryloxyethylphosphonic monophenyl ester.

In the present invention, there is no limitation on the amount of using the phosphoric acid-type monomer (A1) so far as the total valency ratio ($R_E$) is set to lie within a predetermined range. For example, the monomer component (A) may be wholly the phosphoric acid-type monomer (A1) or may be partly the phosphoric acid-type monomer (A1). From such a standpoint that the adhesive composition penetrates into the tooth to a suitable degree and improves the strength of the cured body, however, it is desired to use the polymerizable monomer (A2) without acidic group and the phosphoric acid-type monomer (A1) in combination as the monomer component (A). From the standpoint of obtaining a favorable adhesive strength to both the enamel and the dentin, in particular, it is desired to use the phosphoric acid-type monomer (A1) in an amount of not less than 5 mass % and, more preferably, in a range of 5 to 80 mass % and, most preferably, 10 to 60 mass % per the whole amount of the monomer component (A). If the blended amount of the phosphoric acid-type monomer (A1) is small, the adhesive strength to the enamel tends to decrease. If the amount thereof is large, on the other hand, the adhesive strength to the dentin tends to decrease.

As the polymerizable monomer without acidic group (hereinafter called non-acidic monomer) used in combination with the phosphoric acid-type monomer (A1), there is used a compound having in the molecules thereof at least one polymerizable unsaturated group mentioned above but without acidic group. The following compounds are concrete examples of the non-acidic monomer (A2), which can be used in one kind or in a combination of two or more kinds.

1. Mono(meth)acrylate-type monomers;
methyl(meth)acrylate,
ethyl(meth)acrylate,
glycidyl(meth)acrylate,
2-cyanomethyl(meth)acrylate,
benzyl(meth)acrylate,
polyethylene glycol mono(meth)acrylate,
allyl(meth)acrylate,
2-hydroxyethyl(meth)acrylate,
glycidyl(meth)acrylate,
3-hydroxypropyl(meth)acrylate,
glycelyl mono(meth)acrylate,
2-(meth)acryloxyethylacetyl acetate.
2. Multifunctional (meth)acrylate-type monomers;
ethylene glycol di(meth)acrylate,
diethylene glycol di(meth)acrylate,
triethylene glycol di(meth)acrylate,
nonaethylene glycol di(meth)acrylate, propylene glycol di(meth)acrylate,
dipropylene glycol di(meth)acrylate,
2,2'-bis[4-(meth)acryloyloxyethoxyphenyl]propane,
2,2'-bis[4-(meth)acryloyloxyethoxyethoxyphenyl propane,
2,2'-bis{4-[3-(meth)acryloyloxy-2-hydroxypropoxy] phenyl}propane,
1,4-butanediol di(meth)acrylate,
1,6-hexanediol di(meth)acrylate,
trimethylolpropane tri(meth)acrylate,
urethane(meth)acrylate,
epoxy(meth)acrylate.

As the non-acidic monomer (A2), at least one kind of the polymerizable monomer other than the above (meth)acrylate-type monomers can be used in combination with the (meth)acrylate-type monomer. As the other non-acidic monomers (A2), there can be exemplified fumaric ester compounds such as dimethyl fumarate, diethyl fumarate and diphenyl fumarate; styrene-type derivatives such as styrene, divinylbenzene, α-methylstyrene and α-methylstyrene dimer; and allyl compounds such as diallyl phthalate, diallyl terephthalate, diallyl carbonate and allyl diglycol carbonate.

When a highly hydrophobic polymerizable monomer is used as the non-acidic monomer (A2), it is desired to use amphipatic monomers such as 2-hydroxyethyl(meth)acrylate and 2-hydroxypropyl(meth)acrylate in combination to assure a homogeneous composition preventing the isolation of water to thereby obtain a high adhesive strength.

The dental adhesive composition of the present invention contains the phosphoric acid-type monomer as described above and, usually, exhibits acidic property and, therefore, exhibits demineralizing action due to the acidic component. When the metal ions are released in large amounts from the below-mentioned multivalent metal ion-releasing component (B), however, the dental adhesive composition of the present invention is neutralized with acidic groups, ceases to exhibit acidic property, exhibits decreased demineralizing action and may exhibit decreased adhesive strength and durability of adhesion. In such a case, the acidity is adjusted by using an acidic substance for adjusting pH. The acidic substance for adjusting pH will be described later.

<Multivalent Metal Ion-Releasing Components (B)>

In the present invention, it is important that the phosphoric acid-type monomer (A1) contained in the monomer component (A) is present together with earth metal ions. With the earth metal ions being present together with the phosphoric acid-type monomer, the ionic crosslinking develops to a sufficient degree and a very large adhesive strength is obtained as described already. The present invention uses the multivalent metal ion-releasing component (B) as a source of feeding earth metal ions. That is, the multivalent metal ion-releasing component (B) must at least be capable of releasing earth metal ions.

The above earth metals are metals belonging to the Group 3 and the Group 13 of periodic table as described above, and their concrete examples include rare earth metals such as yttrium, scandium and lanthanoide ions; and aluminum family metals, such as aluminum, gallium and indium. The lanthanoides include lanthanum, cerium, praseodymium, neodymium, promethium, samarium, europium, gadolinium, terbium, dysprosium, holmium, erbium, thulium, ytterbium and lutetium. In the dental composition of the present invention, the ions of at least one kind of the above earth metal are released from the multivalent metal ion-releasing component (B) and are present together with the above phosphoric acid-type monomer (A1). Among the above earth metal ions, what are more effective are aluminum ions and lanthanoide ions. Among them, aluminum ions and lanthanum ions are preferred, and lanthanum ions are most preferred. For example, even when a plurality of kinds of earth metal ions are present together with the phosphoric acid-type monomer (A1), it is desired that part of them are lanthanum ions and, most desirably, not less than 10 mol % of the earth metal ions are lanthanum ions.

In the present invention, the earth metal ions released from the multivalent metal-releasing component (B) and are present together with the phosphoric acid-type monomer (A1) must be in such an amount that the total valency ratio ($R_E$) thereof to the phosphoric acid-type monomer is in a range of 0.2 to 3.0, particularly, 0.3 to 0.9 and, most desirably, 0.4 to 0.7. If the total valency ratio ($R_E$) lies outside the above range, the ionic crosslinking does not develop to a sufficient degree with the acidic groups possessed by the phosphoric acid-type monomer (A1), the demineralizing action (tooth-etching property) decreases, and a desired very large adhesive strength and water resisting property (or durability of adhesion) are spoiled.

Further, so far as the earth metal ions are present in the above amount together with the phosphoric acid-type monomer (A1), the multivalent metal-releasing component (B) may release other metal ions than the above earth metal ions so as to be present therein. Other metal ions may be, for example, monovalent and divalent metal ions, such as alkali metal ions and alkaline earth metal ions or may, further, be trivalent metal ions other than the above earth metal ions, such as iron (III), ruthenium (III) and cobalt (III). Here, however, it is desired that the total ionic valency of these other metal ions contained in the composition is not larger than 0.5 and, particularly, not larger than 0.2 per the total valency of all metal ions (sum of the total valency of the earth metal ions and the total valency of the other metal ions). That is, the total valency ratio ($R_T$) of the metal ions other than the earth metal ions to the whole metal ions is represented by the following formula, $$R_T = TV_M / TV_T \qquad (2)$$

wherein $TV_M$ is a total valency of the metal ions other than the earth metal ions contained in the composition, and
$TV_T$ is a total valency of the whole metal ions contained in the composition, and is desired to lie in a range of not larger than 0.5 and, particularly, not larger than 0.2. This is because if other metal ions are present in large amounts, then development of ionic crosslinking based on the earth metal ions is spoiled due to the neutralizing reaction between the other metal ions and the acidic groups of the phosphoric acid-type monomer.

The total valency ($TV_T$) of the whole metal ions in the formula (2) is calculated according to the following formula (2a), $$TV_T = \Sigma I_k \times B_k \qquad (2a)$$

wherein k is 1, 2, 3, - - - , n, and n is a number of kinds of metal ions contained in the composition,
$I_k$ is a mol number of the metal ions contained in the composition, and
$B_k$ is a valency of the metal ions.

The total valency of the other metal ions or the whole metal ions contained in the composition is calculated in the same manner as the total valency ($TV_E$) of the earth metal ions described above.

Further, incase other metal ions are present in addition to the earth metal ions, if the valency ratio of the whole metal ions to the phosphoric acid-type monomer is not smaller than 1, the acidity of the adhesive composition is impaired, the demineralizing action decreases and the adhesive strength decreases. The same also holds if the total valency ratio ($R_E$)

of the earth metal ions to the phosphoric acid-type monomer is not smaller than 1. In this case, therefore, it becomes necessary to adjust the acidity of the composition by using an acidic substance for adjusting pH that will be described later.

As the multivalent metal ion-releasing component (B) used for the adhesive composition of the present invention to release earth metal ions in such an amount that the total valency ratio ($R_E$) thereof assumes a predetermined value when it is mixed into water together with the phosphoric acid-type monomer (A1), there can be used, for example, a simple earth metal, an earth metal compound and an earth metal ion-eluting filler containing an earth metal. However, the simple earth metal dissolves very little in water, and a very long period of time will be required until the total valency ratio ($R_E$) thereof to that of the phosphoric acid-type monomer (A1) lies in a predetermined range. In the present invention, therefore, the earth metal compound and the earth metal ion-eluting filler are preferably used.

As the earth metal compound, there can be used an acid having a pKa-value at least higher than a pKa-value which is based on a first dissociation of phosphoric acid, i.e., a metal salt which is more weakly acidic than phosphoric acid. This is because, if a salt more strongly acidic than phosphoric acid is used, ionic bond does not occur to a sufficient degree between the free earth metal ions and the acidic groups of the phosphoric acid-type monomer.

As the earth metal salt more weakly acidic than phosphoric acid, there can be exemplified carbonate, enol salt of 1,3-diketone, citrate, tartarate, fluoride, malonate, glycolate, lactate, phthalate, isophthalate, terephthalate, acetate and methoxyacetate. As will be described later, some of these weakly acidic earth metal salts dissolve very little in water. It is, therefore, recommended to confirm the dissolution by conducting experiments in advance and to make sure if ions are released in such amounts as to satisfy a predetermined total valency ratio ($R_E$). As the earth metal compounds, there can be, further, used a hydroxide, a hydride and an alkoxide.

Among the above earth metal compounds according to the present invention, it is desired to use a hydroxide, a hydride, a carbonate or a lower alkoxide having not more than 4 carbon atoms from such a standpoint that the earth metal ions elute out quickly, the by-product is a gas, water or a lower alcohol at normal temperature and, hence, the by-product can be easily removed when the composition is applied to the tooth surfaces without adversely affecting the adhesive strength. From the standpoint of easy handling, further, the hydroxide, alkoxide and carbonate are more preferred.

In the present invention, concrete examples of the earth metal compound that can be particularly preferably used as the multivalent metal ion-releasing component (B) include aluminum methoxide, aluminum isopropoxide, aluminum hydroxide, aluminum acetylacetonato, gallium ethoxide, indium ethoxide, scandium isopropoxide, yttrium isopropoxide, lanthanum methoxide, lanthanum ethoxide, lanthanum isopropoxide, lanthanum hydroxide, lanthanum carbonate, cerium isopropoxide, praseodymium isopropoxide, promethium isopropoxide, neodymium isopropoxide, samarium isopropoxide, europium acetylacetonato, gadolinium acetylacetonato, terbium acetylacetonato, dysprosium acetylacetonato, holmium acetylacetonato, erbium acetylacetonato, thulium acetylacetonato, ytterbium isopropoxide, ytterbium acetylacetonato and lutetium acetylacetonato. Among them, aluminum methoxide, aluminum isopropoxide, aluminum hydroxide, lanthanum methoxide, lanthanum ethoxide, lanthanum isopropoxide, lanthanum hydroxide and lanthanum carbonate are particularly desired.

Many of oxides of aluminum and lanthanum and carbonates are insoluble in a polymerizable monomer or in an organic solvent, and, generally, therefore, require very extended periods of time for eluting the earth metal ions in the above required amounts even in the presence of water, and are not suited as the multivalent metal ion-releasing component (B) which is the source of earth metal ions. In particular, the oxides of aluminum and lanthanum do not almost elute out their metal ions even in the presence of water, and cannot be used as the multivalent metal ion-releasing component (B).

Further, the earth metal ion-eluting filler containing an earth metal is capable of eluting out the earth metal ions in the dental adhesive composition that exhibits acidic property but does not substantially elute out strongly acidic conjugated base ions having a pKa-value lower than a pKa-value based on a first dissociation of phosphoric acid. The filler, in general, comprises glasses (e.g., oxide glass, fluoride glass) having a chain-like, laminar or mesh-structured skeleton holding at least earth metal ions in the gaps of the skeleton. For example, there can be preferably used an oxide glass such as aluminosilicate glass or borosilicate glass, and a fluoride glass such as zirconium fluoride glass containing earth metal ions. It is, further, allowable to use a soda lime glass containing earth metal ions.

In the earth metal ion-eluting filler comprising these glasses, the residual components remaining after the earth metal ions are eluted out are, generally, porous particles which, if allowed to remain in the composition, serve as a reinforcing material contributing to improving the strength of the cured body. However, if the residual components aggregate together or have large particle sizes to precipitate in the composition, then the residual components can be removed by filtering as required.

Among the earth metal ion-eluting fillers of the present invention, the aluminosilicate glass is particularly desired. Most desirably, a fluoroaluminosilicate glass having the so-called fluorine gradually-releasing property is used gradually releasing fluoride ions that work to strengthen the tooth after the adhesion.

The above fluoroaluminosilicate glass that is preferably used will be a widely known one that is used, for example, for the glass ionomer cement. The fluoroaluminosilicate glass contains aluminum in large amounts as the earth metal and often contains lanthanum and other earth metals as well. The fluoroaluminosilicate that is usually used has the following composition.

Composition of the fluoroaluminosilicate glass:
Silicon: 5 to 33 mass %
Aluminum: 10 to 30 mass %
Lanthanum: 7 to 30 mass %
Calcium: 1 to 17 mass %
Sodium: 0 to 2 mass %
Phosphorus: 0.2 to 16 mass %
Fluorine: 2 to 40 mass %
Oxygen: balance The fluoroaluminosilicate glass that is most desirably used in the present invention has the following composition:
Silicon: 5 to 33 mass %
Aluminum: 10 to 30 mass %
Lanthanum: 10 to 30 mass %
Calcium: 1 to 3 mass %
Sodium: 0 to 1 mass %
Phosphorus: 0.5 to 5 mass %
Fluorine: 5 to 20 mass %
Oxygen: balance There can be, further, preferably used the one in which aluminum is partly replaced by other earth metals such as scandium, yttrium, ytterbium, etc.

The fluoroaluminosilicate glass that is used as the earth metal ion-eluting filler which is the component (B) contains fluoride ions in considerably large amounts to elute out and react with water in the system and to form a hydrogen fluoride. Here, however, the fluorine ions are not the strongly acidic conjugated base ions having a pKa-value lower than a pKa-value based on the first dissociation of phosphoric acid but are conjugated base ions which are more weakly acidic than phosphoric acid. Therefore, there is no problem if they are contained in the composition, and the acidity of the adhesive composition may be adjusted depending upon the amount of elution thereof by using an acidic substance for adjusting pH that will be described later.

In the present invention, there is no particular limitation on the shape of particles of the multivalent metal ion-releasing component (B) which is the earth metal ion-eluting filler; i.e., the particles may be of a milled particulate shape as obtained through an ordinary milling, a spherical particulate shape or, as required, a mixture of plate-like particles and fibrous particles.

<Water (C)>

In the present invention, in order for the multivalent metal ion-releasing component (B) to release earth metal ions of a predetermined amount, water is necessary as a component (C). This is because without water, ions of earth metals are not released even if the component (B) is contained in large amounts.

In the present invention, when the adhesive composition of the present invention is applied to the surface of the tooth, it is desired that the water is removed by blowing the air prior to curing the composition from the standpoint of conducting the curing to a sufficient degree. After the earth metal ions have been eluted out, further, water can be removed from the composition by distillation under reduced pressure.

Water is present to some extent in an environment in the oral cavity where the dental adhesive composition of the present invention is applied. Even when no water is contained, therefore, the adhesive composition of the present invention works to delime the tooth due to the predetermined demineralizing action of the dental adhesive composition, and a favorable adhesive force is obtained. To delime the tooth to a more sufficient degree, however, it is desired that water is contained.

In the present invention, water (C) is used in an amount of 3 to 150 mass parts and, particularly, 5 to 100 mass parts per 100 mass parts of the polymerizable monomer component (A).

<Fumed Silica (D)>

It is desired that the dental adhesive composition of the present invention is, further, blended with fumed silica as a component (D) in addition to the above components (A) to (C). That is, addition of the fumed silica helps greatly enhance the strength and water resisting property of the cured body obtained by curing the adhesive composition. When used as an adhesive or a pretreating agent at the time of adhering the prosthetic material to the tooth, therefore, resistance is conspicuously improved against the tensile stress that occurs in the interface between the prosthetic material and the tooth. Besides, resistance is further improved against the force produced by the occlusion of teeth after the prosthetic material has been adhered and fixed to the restored part of the tooth. Therefore, the prosthetic material is held maintaining stability for extended periods of time.

Though the reason has not yet been correctly clarified why the cured body exhibits very increased strength when it is blended with the fumed silica (D), the present inventors presume as described below.

That is, upon being blended with the fumed silica in the presence of water, it is presumed that the ionically crosslinked polymer infiltrates into gaps among aggregated particles of the fumed silica, entangles with the fumed silica, and the silanol groups present on the surfaces of the fumed silica particles bond to multivalent metal ions present in the composition via water. Therefore, it is presumed that a strong network of fumed silica is highly densely formed in the cured body and, as a result, the adhesive strength is very increased, the water resisting property is further improved, and excellent durability is obtained over extended periods of time.

Here, the fumed silica is amorphous silica produced by a flame hydrolysis method, and is, concretely, produced by hydrolyzing a silicon tetrachloride at a high temperature in the oxyhydrogen flame. The fumed silica produced by the above method comprises fine particles having an average primary particle size ($D_{50}$) of about 5 to 100 nm calculated as a volume as measured by a laser diffraction scattering method, and has a mild three-dimensionally aggregated structure. That is, with the aggregated structure of fine particles being entangled with the ionically crosslinked cured body in a complex manner via water, a strong and highly dense network is formed realizing a very large adhesive strength. For example, when there is used silica other than the fumed silica obtained by other method such as wet method, sol-gel method or flame molten method, or inorganic filler other than silica, a mild three-dimensional aggregated structure is not formed in the adhesive composition. Therefore, the above-mentioned network is not formed, and the adhesive strength is not greatly improved as when the fumed silica is used.

Though there is no particular limitation, the present invention, usually, uses the fumed silica having a BET specific surface area of not smaller than 70 $m^2/g$ and, particularly, in a range of 100 to 300 $m^2/g$. From the standpoint of forming the network by bonding with the above multivalent metal ions, further, it is desired that the silanol groups are present in a suitable amount on the surface. For example, the fumed silica having silanol groups present on the surface at a rate of not less than 0.1 group/$nm^2$ and, particularly, 0.5 to 2 groups/$nm^2$ is preferably used. The number of silanol groups on the surface of the fumed silica may be measured by a Carl-Fischer method by once dipping the fumed silica in water followed by drying at 150° C.

Further, the number of silanol groups on the surfaces of the fumed silica can be adjusted by treating the surfaces with a surface-treating agent as represented by a silane coupling agent. As the silane coupling agent, there can be preferably used methyltrimethoxysilane, methyltriethoxysilane, methyltrichlorosilane, dimethyldichlorosilane, trimethylchlorosilane, hexamethyldisilazane, vinyltrimethoxysilane, vinyltriethoxysilane, vinyltrichlorosilane, vinyltriacetoxysilane, vinyltris(β-methoxyethoxy)silane, γ-methacryloyloxypropyltrimethoxysilane, γ-methacrloyloxypropyltris(β-methoxyethoxy) silane, γ-chloropropyltrimethoxysilane, γ-chloropropylmethyldimethoxysilane, γ-glycidoxypropyltrimethoxysilane, γ-glycidoxypropylmethyldiethoxysilane, β-(3,4-epoxycyclohexyl)ethyltrimethoxysilane, N-phenyl-γ-aminopropyltrimethoxysilane and hexamethyldisilazane. Particularly preferably, methyltrichlorosilane, dimethyldichlorosilane and hexamethyldisilazane are used.

Though there is no particular limitation, it is desired that the fumed silica is added in an amount of 0.5 to 20 mass parts and, particularly, 5 to 10 mass parts per 100 mass parts of the monomer component (A) from the standpoint of improving the adhesive strength, suppressing the viscosity of the composition to lie in a predetermined range and maintaining permeability into the tooth.

<Polymerization Initiator (E)>

The adhesive composition of the present invention may be blended with an effective amount of a polymerization initiator (E). When used as a dental adhesive, in particular, it is necessary to add a polymerization initiator thereto.

A desired polymerization initiator (E) is a photopolymerization initiator since it is capable of effecting the polymerization and curing at any timing. As the photopolymerization initiator, there is used a compound which by itself forms radical species upon being irradiated with light, or a mixture of this compound to which a polymerization promoter is added.

Described below are examples of the compound which by itself undergoes the decomposition upon being irradiated with light and forms polymerizable radical species.

α-Diketones
camphorquinone, benzyl, α-naphthyl, acetonaphthene, naphthoquinone, 1,4-phenanthrenequinone, 3,4-phenanthrenequinone, 9,10-phenanthrenequinone, etc.

Thioxanthones:
2,4-diethylthioxanthone, etc.

α-Aminoacetophenones:
2-benzyl-dimethylamino-1-(4-morpholinophenyl)-butanone-1,
2-benzyl-diethylamino-1-(4-morpholinophenyl)-butanone-1,
2-benzyl-dimethylamino-1-(4-morpholinophenyl)-propanone-1,
2-benzyl-diethylamino-1-(4-morpholinophenyl)-propanone-1,
2-benzyl-dimethylamino-1-(4-morpholinophenyl)-pentanone-1,
2-benzyl-diethylamino-1-(4-morpholinophenyl)-pentanone-1.

Acylphosphinoxide Derivatives:
2,4,6-trimethylbenzoyldiphenylphosphinoxide,
bis(2,6-dimethoxybenzoyl)-2,4,4-trimethylpentylphosphinoxide.

As the above polymerization promoter, there can be used tertiary amines, barbituric acids and mercapto compound. Described below are concrete examples thereof.

Tertiary amines:
N,N-dimethylaniline,
N,N-diethylaniline,
N,N-di-n-butylaniline,
N,N-dibenzylaniline,
N,N-dimethyl-p-toluidine,
N,N-diethyl-p-toluidine,
N,N-dimethyl-m-toluidine,
p-bromo-N,N-dimethyaniline,
m-chloro-N,N-dimethylaniline,
p-dimethylaminobenzaldehyde,
p-dimethylaminoacetophenone,
p-dimethylaminobenzoic acid,
ethyl ester of p-dimethylaminobenzoic acid,
amyl ester of p-dimethylaminobenzoic acid,
methyl ester of N,N-dimethylanthranic acid,
N,N-dihydroxyethylaniline,
N,N-dihydroxyethyl-p-toludine,
p-dimethylaminophenyl alcohol,
p-dimethylaminostilbene,
N,N-dimethyl-3,5-xylidine,
4-dimethylaminopyridine,
N,N-dimethyl-α-naphthylamine,
N,N-dimethyl-β-naphthylamine,
tributylamine,
tripropylamine,
triethylamine,
N-methyldiethanolamine,
N-ethyldiethanolamine,
N,N-dimethylhexylamine,
N,N-dimethyldodecylamine,
N,N-dimethylstearylamine,
N,N-dimethylaminoethyl acrylate,
N,N-dimethylaminoethyl methacrylate,
2,2'-(n-butylimino)diethanol.

Barbituric Acids:
5-butylbarbituric acid,
1-benzyl-5-phenylbarbituric acid.

Mercapto Compounds:
dodecyl mercaptane,
pentaerythritoltetrakis(thioglycolate).

Though there is no particular limitation, the polymerization initiator (E) is added in an amount effective for curing the adhesive composition, and its amount may be suitably set. Generally, however, the polymerization initiator (E) is used in an amount in a range of 0.01 to 10 mass parts and, particularly, 0.1 to 5 mass parts per 100 mass parts of the monomer component (A). If the amount thereof is less than 0.01 mass parts, the polymerization becomes insufficient. If the amount thereof exceeds 10 mass parts, the strength of the cured body tends to decrease.

<Acidic Substances for Adjusting pH>

As described already, the dental adhesive composition of the present invention contains a phosphoric acid-type monomer (A1) having an acidic group as the monomer component (A) and, therefore, usually, exhibits acidic property and exhibits demineralizing action due to the presence of the acidic component, and highly penetrates into the tooth. That is, the fact that dental adhesive composition of the present invention that exhibits acidic property, is one of the factors that indicate that the composition has a high adhesive strength lending itself well suited for use as an adhesive obviating the need of etching the tooth and, further, lending the composition itself well suited for use as a pretreating agent. To utilize the above advantages to a maximum degree, therefore, it is desired that the composition of the present invention has a high acidity, e.g., has a pH of not higher than 4.8 and, preferably, in a range of 0.5 to 4.0 and, particularly preferably, 1.0 to 3.0.

Here, the pH of the adhesive composition is a value measured at 25° C. by mixing the adhesive composition at a concentration of 10 mass % into ethanol and by using a pH meter that uses a pH electrode calibrated by using a neutral phosphate pH standard solution (pH 6.86) and a phthalate pH standard solution (pH 4.01). Ethanol used for the dilution should have a purity of not lower than 99.5%, and a pH value by ethanol alone of 4.8 to 5.0.

Here, if the multivalent metal ion-releasing component (B) releases earth metal ions in large amounts causing the total valency ratio ($R_E$) thereof to the phosphoric acid-type monomer (A1) to become not less than 1, then the acidic group of the phosphoric acid-type monomer bonds to the earth metal ion so that no acidic property is exhibited bringing about such inconveniences as deteriorated demineralizing property and decreased adhesive strength. This holds quite the same even when the amount of the total metal ions released from the components so increases that the total valency ratio of the total metal ions to the phosphoric acid-type monomer (A1)

becomes not less than 1. In such a case, it becomes necessary to adjust the pH by adding an acidic substance other than the phosphoric acid-type monomer (A1) so that the pH of the composition lies, for example, in the above-mentioned range.

As the acidic substance for adjusting the pH, the present invention uses a substance of which the pKa-value exceeds 2.15 in water of 25° C., i.e., a substance that is more weakly acidic than phosphoric acid. This is because if there is used a substance more strongly acidic than phosphoric acid, then no ionic crosslinking is formed between the earth metal ion and the phosphoric acid-type monomer. From the standpoint of a strong demineralizing function to the tooth, furthermore, it is desired that the acidic substance has a pKa-value which is not larger than 6.0 and, particularly, not larger than 4.0. Suitable examples of the acidic substance for adjusting pH include citric acid, tartaric acid, hydrofluoric acid, malonic acid, glycolic acid, lactic acid, phthalic acid, isophthalic acid, terephthalic acid and methoxyacetic acid.

As the acidic substance for adjusting pH, further, there can be used a polymerizable monomer having an acidic group other than the acidic group derived from phosphoric acid and having the above pKa-value to substitute for part of the above non-acidic monomer (A2). As the polymerizable monomer used for adjusting pH, there can be exemplified 2-(6-methacryloxyhexyl) malonic acid, 2-(10-methacryloxydecyl)malonic acid, trimellitic acid-4-(2-methacryloxyethyl)ester, N-methacryloylglutamic acid, 1,2,4,5-benzenetetracarboxylic acid-2,4-bis(2-methacryloxyethyl)ester, and 3,3,4,4-biphenyltetracarboxylic acid-4,4-bis(2-methacryloxyethyl)ester.

In using the acidic substance other than the above phosphoric acid-type monomer (A1) for adjusting pH, if the acidic substance is used in an unnecessarily large amount, it may become difficult to form the ionic crosslinking between the earth metal ion and the acidic group of the phosphoric acid-type monomer (A1). Therefore, when pH is to be adjusted by using the acidic substance, it is desired that the phosphoric acid-type monomer (A1) is used in an amount of not less than 20 mol % and, preferably, not less than 40 mol % per the whole acidic substances (phosphoric acid-type monomer+ other acidic substances).

<Other Blending Agents>

The dental adhesive composition of the present invention may contain various blending agents that have been known in the dental field in addition to the above-mentioned components in a range in which they do not deteriorate the properties of the dental adhesive composition.

In addition to the above polymerization initiator (E), for example, the dental adhesive composition may be blended with an electron acceptor such as iodonium salt, trihalomethyl-substituted S-triazine or phenanthrylphosphonium salt compound. Addition of the electron acceptor enhances the polymerizing activity.

Further, when used as a dental adhesive, there can be used, in addition to the fumed silica (D), an inorganic filler such as silica other than fumed silica, as well as zirconia, titania, silica/zirconia or silica/titania. The inorganic filler is used for improving the mechanical strength and water resisting property, and can be, further, used being treated for its surface with the above silane coupling agent so as to be hydrophobic. Upon being treated to be hydrophobic, affinity to the monomer component (A) enhances making it possible to further increase the mechanical strength and water resisting property.

The inorganic filler other than the fumed silica is, usually, added in an amount of 2 to 400 parts by mass and, particularly, 5 to 100 parts by mass per 100 parts by mass of the monomer component (A). When the adhesive composition is used as an adhesive for a composite resin, in particular, it is desired that the inorganic filler is added in an amount of 2 to 20 parts by mass and, particularly, 5 to 10 parts by mass to the composition.

It is also allowable to add a volatile water-soluble organic solvent in order to adjust the viscosity of the adhesive composition or to homogeneously disperse the monomer component (A) in the composition. That is, the organic solvent has a boiling point under 760 mmHg of not higher than 100° C., a vapor pressure at 20° C. of not lower than 1.0 kPa, and a solubility in water at 20° C. of not less than 20 g/100 ml. As the volatile water-soluble organic solvent, there can be exemplified methanol, ethanol, n-propanol, isopropyl alcohol, acetone and methyl ethyl ketone. As required, a plurality of these organic solvents may be used being mixed together. By taking toxicity to the living body into consideration, however, it is desired to use ethanol, isopropyl alcohol or acetone.

The amount of the volatile organic solvents may vary depending upon the kind and amount of the monomer component (A) that is used but is, usually, 2 to 400 parts by mass and, particularly, 5 to 100 parts by mass per 100 parts by mass of the monomer component (A).

Like water, these volatile organic solvents, too, are removed by blowing the air when the adhesive composition of the invention is applied onto the tooth surface prior to curing the adhesive composition.

In addition to the above blending agents, there can be further added as required an organic viscosity-increasing agent of such a high molecular compound as polyvinylpyrrolydone, carboxymethyl cellulose or polyvinyl alcohol. Moreover, various additives may be added as required, such as ultraviolet-ray absorber, dye, antistatic agent, pigment, perfume and the like.

<Preparation of Dental Composition and Use>

The dental adhesive composition of the present invention is produced by homogeneously mixing the above-mentioned components together and, thereafter, adjusting the concentration of earth metal ions to lie in a predetermined range.

This composition contains acidic substances such as the phosphoric acid-type monomer (A1) and the acidic substance for adjusting pH. As described already, however, use is not made of an acidic substance more strongly acidic than phosphoric acid or, concretely, strong acid having a pKa-value lower than the pKa-value (2.15) based on the first dissociation of phosphoric acid in water of 25° C. That is, the adhesive strength of the cured body decreases if conjugated base ions of such a strong acid are contained in the adhesive composition. The conjugated base ions of such a strong acid ionically bonds to the acidic groups possessed by the phosphoric acid-type monomer (A1) competing with the earth metal ions suppressing, therefore, the formation of ionic crosslinking between the earth metal ion and the acidic group.

As the strong acid having the above pKa-value, there can be representatively exemplified such inorganic acids as hydrochloric acid, bromic acid, iodic acid, sulfuric acid and nitric acid; and such organic acids as alkylsulfuric acid and sulfonic acid. Representative examples of the conjugated base ions corresponding to these strong acids include such inorganic acid ions as chloride ions, bromide ions, iodide ions, sulfuric acid ions and nitric acid ions; and such organic acid ions as alkylsulfuric acid ions and sulfonic acid ions.

Therefore, the dental adhesive composition of the invention contains the conjugated base ions of the strong acid in limited amounts, e.g., contains in amounts not larger than 5 mol %, particularly, not larger than 3 mol % with respect to the earth metal ions and, most desirably, does not substantially contain the conjugated base ions of the strong acid.

In the present invention, whether the conjugated base ions of the strong acid are contained in the composition can be confirmed by taking a measurement using an ion chromatography. Concretely, the adhesive composition is extracted with water, the obtained aqueous phase is filtered, and the filtrate is measured by using the ion chromatography to confirm.

The multivalent ion-releasing component (B) is used in such an amount that the total valency ratio ($R_E$) of the amount of the released earth metal ions to the phosphoric acid-type monomer (A1) is in the above-mentioned range (0.2 to 3.0). By simply mixing the components, however, the total valency ratio ($R_E$) does not reach the above range and, therefore, aging must be effected for a predetermined period of time. This is because a certain period of time is required until a predetermined amount of earth metal ions are released after the multivalent ion-releasing component (B) is mixed with the other component containing water. In the present invention, in particular, an earth metal ion-eluting filler containing an earth metal is preferably used as the multivalent ion-releasing component (B) from such a standpoint that residual components contribute to improving the strength. The earth metal ion-eluting filler, however, requires not less than 10 hours before a predetermined amount of earth metal ions are released. Depending upon the kind and amount of the multivalent ion-releasing component (B), therefore, it becomes necessary to effect aging until the total valency ratio ($R_E$) reaches a predetermined value.

The above aging is, usually, achieved if the composition prepared by mixing all components together is left to stand at room temperature. When, for example, a fluoroaluminosilicate glass is used as the component (B), the aging time under a room temperature condition is at least 12 hours. When a salt of an earth metal is used, further, the aging time may be as relatively short as several minutes. The aging time can be further shortened by heating the composition at a suitable temperature (e.g., about 30 to 40° C.).

Through the above aging, the dental adhesive composition of the present invention can be used as an adhesive for adhering a dental restorative such as a composite resin or a prosthetic material to the tooth, as an adhesive for adhering an instrument for correcting irregular teeth such as a bracket to the tooth surfaces, and as a dental pre-treating material owing to its tooth-demineralizing function without blended with the polymerization initiator (E).

The dental adhesive composition of the present invention may undergo a gelation if a long period of time passes after the total valency ratio ($R_E$) of the earth metal ions has reached a predetermined value. After the total valency ratio ($R_E$) of the earth metal ions has reached the predetermined value, therefore, it is desired that the dental adhesive composition of the present invention is put to use as, for example, the adhesive or the pre-treating agent as early as possible before the gelation takes place.

EXAMPLES

The invention will now be concretely described by way of Experimental Examples to which only, however, the invention is in no way limited.

Experimental Example (I) is for demonstrating that a desired adhesive strength is obtained when the total valency ratio ($R_E$) of the earth metal ions to the phosphoric acid monomer (A1) is set to lie in a predetermined range, and Experimental Example (II) is for demonstrating the effect for improving the adhesive strength of when the adhesive composition of the invention is blended with a fumed silica.

Described below are abbreviations, symbols, method of measuring the adhesive strength, method of evaluating preservation stability and method of measuring the amount of multivalent metal ions in Experimental Examples.

Polymerizable Monomer Components (A)

[Phosphoric Acid-Type Monomers (A1)]
 PM1: 2-methacryloyloxyethyldihydrogen phosphate
 PM2: bis(2-methacryloyloxyethyl)hydrogen phosphate
 PM: mixture of PM1 and PM2 at 2:1
 MDP: 10-methacryloyloxydecyldihygrogen phosphate
 HP:

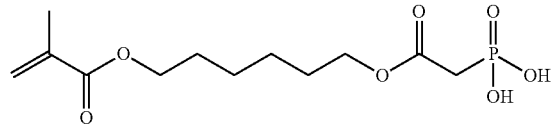 [SMILES: C=C(C)C(=O)OCCCCCCOC(=O)CP(=O)(O)O]

[Other Acidic Group-Containing Polymerizable Monomers]
 MAC-10:

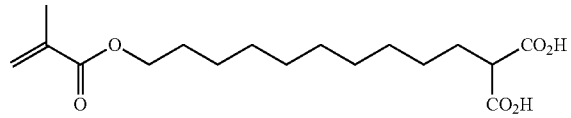 [SMILES: C=C(C)C(=O)OCCCCCCCCCCC(C(=O)O)C(=O)O]

[Polymerizable Monomers without Containing Acidic Group (A2)]
 BisGMA: 2,2'-bis[4-(2-hydroxy-3-methacryloxypropoxy) phenyl]propane
 3G: triethylene glycol dimethacrylate
 HEMA: 2-hydroxyethyl methacrylate Multivalent Metal Ion-Releasing Components (B)
 Al(O-i-Pr)$_3$: aluminum triisoproxide
 Al(OH)$_3$: aluminum hydroxide
 La(O-i-Pr)$_3$: lanthanum triisopropoxide
 La(OH)$_3$: lanthanum hydroxide
 Sc(O-i-Pr)$_3$: scandium triisopropoxide
 Yb(O-i-Pr)$_3$: ytterbium triisopropoxide
 Mg(OH)$_2$: magnesium hydroxide
 Ca(OH)$_2$: calcium hydroxide
 Ba(OH)$_2$: barium hydroxide
 Ti(O-i-Pr)$_4$: titanium tetraisopropoxide
 Zr(O-i-Pr)$_4$: zirconium tetraisopropoxide
 V(acac)$_3$: vanadium (III) tetrakisacetylacetonato
 Cr(O-i-Pr)$_3$: chromium (III) triisopropoxide
 Mn(acac)$_3$: manganese (III) tetrakisacetylacetonato
 Fe(OEt)$_3$: iron (III) ethoxide
 Co(acac)$_3$: cobalt (III) tetrakisacetylacetonato
 Ni(acac)$_2$: nickel(II) tetrakisacetylacetonato
 Cu(OEt)$_2$: copper (II) ethoxide
 W(OEt)$_6$: tungsten (VI) ethoxide
 Zn(OCH$_2$CH$_2$OMe)$_2$: zinc bis(2-methoxyethoxide)
 Al$_2$O$_3$: aluminum oxide particles (average particle size, 13 nm)
 Al(sal)$_3$: aluminum salicylate
 AlCl$_3$: aluminum chloride
 MF: earth metal ion-eluting filler obtained by milling a fluoroaluminosilicate glass powder (Tokuso Ionomer, manufactured by Tokuyama Dental Co.) into an average particle size of 0.5 μm by using a wet-type continuous ball mill (New My-Mill, manufactured by Mitsui Kozan Co.), and treating the filler surfaces with 20 g of 5.0-N hydrochloric acid per gram of the powder for 15 minutes.

Average particle size: 0.5 μm
Amount of ions eluted in 24 hours: 27 meq/g of filler
[Volatile Water-Soluble Organic Solvent]
  IPA: isopropyl alcohol
[Polymerization Initiators]
  CQ: camphor quinone
  DMBE: ethyl p-N,N-dimethylaminobenzoate
  TPO: 2,4,6-trimethylbenzoyldiphenylphosphinoxide
  BTPO: bis(2,4,6-trimethylbenzoyl)-phenylphosphinoxide
[Polymerization Inhibitor]
  BHT: 2,6-di-t-butyl-p-cresole
[Fumed Silica]
  FS1: untreated fumed silica,
    average primary particle size, 18 nm
    specific surface area, 220 m$^2$/g
    number of silanol groups, 5/nm$^2$
  FS2: fumed silica treated with methyl trichlorosilane,
    average primary particle size, 18 nm
    specific surface area, 120 m$^2$/g
    number of silanol groups, 1.2/nm$^2$
  FS3: fumed silica treated with dimethyl dichlorosilane and hexamethyl disilazane,
    average primary particle size, 18 nm
    specific surface area, 200 m$^2$/g
    number of silanol groups, 1/nm$^2$
  FS4: fumed silica treated with methyl trichlorosilane,
    average primary particle size, 40 nm
    specific surface area, 50 m$^2$/g
    treated with methyl trichlorosilane,
    number of silanol groups, 1.3/nm$^2$
  FS5: fumed silica treated with dimethyl dichlorosilane and silicone oil,
    average primary particle size, 18 nm
    specific surface area, 200 m$^2$/g
    number of silanol groups, 0.3/nm$^2$
[Other Inorganic Fillers]
  MS: molten silica treated with 3-methacryloxypropyl trimethoxysilane,
    average primary particle size, 0.4 nm
    specific surface area, 8 m$^2$/g
    number of silanol groups, 2/nm$^2$
  SS: sol/gel silica treated with 3-methacryloxypropyl trimethoxysilane,
    average primary particle size, 60 nm
    specific surface area, 70 m$^2$/g
    number of silanol groups, 3/nm$^2$
  PS: precipitated silica treated with 3-methacryloxypropyl trimethoxysilane,
    average primary particle size, 30 nm
    specific surface area, 180 m$^2$/g
    number of silanol groups >5/nm$^2$
  MF1: multivalent metal filler obtained in Preparation Example 1
    average particle size: 0.5 μm,
    amount of ions eluted in 24 hours: 10 meq/g of filler,
  MF2: multivalent metal filler obtained in Preparation Example 2,
    average particle size: 0.5 μm,
    amount of ions eluted in 24 hours: 25 meq/g of filler,
  MF3: multivalent metal filler obtained in Preparation Example 3,
    average particle size: 0.5 μm,
    amount of ions eluted in 24 hours: 50 meq/g of filler.
In the Experimental Examples, measurements were taken in a manner as described below.

(1) Measurement of Metal Ions:
Various components were mixed together to prepare a sample adhesive composition which was then stirred for 24 hours. 0.2 Grams of the composition was taken into a 100-ml sample tube and was diluted with IPA to be 1 mass %. The solution was filtered through a syringe filter, and the filtrate was measured for the concentrations of metal ions (mmols/g) contained in one gram of the polymerizable monomer relying upon the ICP (induction-coupled plasma) emission spectroanalysis.

(2) Measurement of Phosphoric Acid-Type Monomers:
The IPA solution used for the measurement of the amounts of metal ions was measured with the HPLC in order to measure the concentration of the phosphoric acid-type monomer (mmols/g) contained in one gram of the polymerizable monomer.

From the concentrations of the metal ions and the concentration of the phosphoric acid-type monomer measured above, the total valency ratio ($R_E$) of the earth metal ions and the total valency ratio ($R_T$) of the total metal ions in the compositions were calculated in accordance with the above-mentioned formulas (1) and (2).

(3) Measurement of Anions.
2 Grams of the sample adhesive composition, 100 g of water and 10 g of diethyl ether were vigorously mixed together, left to stand still, the aqueous phase thereof was filtered through the syringe filter, and the obtained filtrate was measured by using an ion chromatography to measure the concentration of anions (mmols/g) contained in one gram of the polymerizable monomer.

(4) Measurement of pH of the Adhesive Composition.
2 Grams of the sample adhesive composition was mixed into 8 g of anhydrous ethanol and was quickly measured for its pH by using a pH electrode (GTS-5211C, manufactured by To a DKK Co.) calibrated with a neutral phosphate pH standard solution (pH 6.86) and a phthalate pH standard solution (pH 4.01).

(5) Adhesion Durability Test.
(a) Method of Preparing an Adhesion Test Piece I (for Evaluation As a Dental Adhesive).

Within 24 hours after the slaughter, a bovine foretooth was pulled out, and the enamel surface and the dentin surface were ground by using a #600 emery paper while pouring water so as to be in parallel with the labial face to thereby prepare a tooth for testing the strength.

Next, the compressed air was blown onto the above surface of the tooth for testing the strength for about 10 seconds to dry the surface and, thereafter, a double-sided adhesive tape having a hole of 3 mm in diameter perforated therein was fixed to either the enamel surface or the dentin surface. Next, a paraffin wax of a thickness of 0.5 mm having a hole of 8 mm in diameter perforated therein was fixed onto the above hole in concentric therewith to form a mimic cavity.

A sample adhesive composition was applied into the mimic cavity, left to stand for 20 seconds and, thereafter, the compressed air was blown thereto for about 10 seconds to dry the composition followed by the irradiation with light from a dental visible ray irradiator (Tokuso Powerlight, manufactured by Tokuyama Co.) for 10 seconds. Further, a dental composite resin (Estelite Σ, manufactured by Tokuyama Dental Co.) was applied thereon, and was irradiated with light from the visible ray irradiator for 30 seconds to prepare a test piece I for evaluating the adhesive.

(b) Method of Preparing an Adhesion Test Piece II (for Evaluation as a Pretreating Agent).
A sample adhesive composition was applied into a mimic cavity in the tooth for testing the strength formed above and after left to stand for 20 seconds, the compressed air was blown thereto for about 10 seconds to dry the composition. Thereafter, an adhesive for two-step composite resin (bonding agent of Tokuso Macbond II, manufactured by Tokuyama Co.) was applied thereon and was irradiated with light from the dental visible ray irradiator (Tokuso Powerlight, manufactured by Tokuyama Co.) for 10 seconds. Further, a dental composite resin (Estelite Σ, manufactured by Tokuyama Dental Co.) was applied thereon, and was irradiated with light from the visible ray irradiator for 30 seconds to prepare a test piece II for evaluating the pretreating agent.

(c-1) Adhesion Test A.

The test piece I for evaluating the adhesive or the test piece II for evaluating the pretreating agent was introduced into a heat shock tester, dipped in a water vessel maintained at 4° C. for one minute, transferred into a water vessel maintained at 60° C. where it was dipped therein for one minute, and was returned again into the water vessel maintained at 4° C. The above operation was repeated 3000 times.

Thereafter, the test piece was pulled by using a tension tester (Autograph manufactured by Shimazu Seisakusho Co.) at a crosshead speed of 2 mm/min. to measure the tensile adhesive strength between the enamel or the dentin and the composite resin. Four test pieces were measured for their adhesive strength per a test relying upon the above method, and an average value thereof was regarded as an adhesive strength after the durability testing to evaluate the durability of adhesion.

(c-2) Adhesion Test B.

The adhesive strength after the durability test was measured in the same manner as in the adhesion test A but repeating 6000 times the operation of introducing the test piece I for evaluating the adhesive or the test piece II for evaluating the pretreating agent into the heat shock tester, dipping the test piece in the water vessel maintained at 4° C. for one minute, transferring the test piece into the water vessel maintained at 60° C. where it was dipped therein for one minute and returning the test piece again into the water vessel maintained at 4° C. in order to evaluate the durability of adhesion under a severer environment.

Experimental Example (I)

Example 1

1.5 Grams of PM (phosphoric acid-type monomer), 3.0 g of BisGMA, 2.0 g of 3G and 3.5 g of HEMA were used as the polymerizable monomer components (A), 0.4 g of aluminum isopropoxide was used as the earth metal ion source (B) and, further, 0.1 g of camphor quinone and 0.15 g of DMBE were used as the polymerization initiators (E). The above components, 8.5 g of IPA (organic solvent), 1.5 g of distilled water (C) and 0.03 g of BHT (polymerization inhibitor) were mixed together and stirred for 24 hours to prepare a dental adhesive composition (adhesive for composite resin) of the present invention.

Relying upon the above-mentioned method, the adhesive composition was measured concerning pH, phosphoric acid-type monomer, metal ions and anions. Further, a test piece I for evaluating the adhesive was prepared according to the above method, and was evaluated for its durability of adhesion to the enamel and the dent in accordance with the adhesion test A. The composition of the adhesive composition is shown in Table 1 and the results of evaluation are shown in Table 2.

Examples 2 to 20

Adhesive compositions (adhesives for composite resin) of compositions shown in Table 1 were prepared according to the method of Example 1, measured in the same manner as in Example 1 and were evaluated for their durability of adhesion according to the adhesion test A. The results were as shown in Table 2.

Example 21

1.5 Grams of PM was used as the phosphoric acid-type monomer (A1) and 1.0 g of fluoroaluminosilicate glass was used as the earth metal ion source (B). These components were mixed with 8.5 g of IPA (organic solvent), 1.5 g of distilled water (C) and 0.03 g of BHT (polymerization inhibitor) and were stirred for 24 hours.

Next, water and IPA were distilled off by using a rotary evaporator, followed by drying under reduced pressure by using a vacuum pump for 2 hours. To the obtained dried product were added 3.0 g of BisGMA, 2.0 g of 3G and 3.5 g of HEMA as the polymerizable monomer components (A), as well as 0.1 g of camphor quinone, 0.15 g of DMBE and 10.0 g of IPA (organic solvent), followed by stirring until the mixture became homogeneous to thereby prepare an adhesive composition (adhesive for composite resin).

The adhesive composition was measured in the same manner as in Example 1 and was evaluated for its durability of adhesion according to the adhesion test A. The composition was as shown in Table 1 and the evaluated results of the durability of adhesion were as shown in Table 2.

Comparative Examples 1 to 26

Adhesive compositions (adhesives for composite resin) of compositions shown in Table 3 were prepared according to the method of Example 1, measured in the same manner as in Example 1 and were evaluated for their durability of adhesion according to the adhesion test A. The results of evaluation were as shown in Table 4.

Comparative Example 27

An adhesive composition of the same composition as that of Example 12 was prepared in quite the same manner as in Example 12 but changing the time for mixing and stirring the components from 24 hours to 1 hour. The adhesive composition was measured in the same manner as in Example 1 and was evaluated for its durability of adhesion according to the adhesion test A. The composition was as shown in Table 3 and the evaluated results of the durability of adhesion were as shown in Table 4.

TABLE 1

| | Adhesive for composite resin (mass parts)[1] | | | | | |
|---|---|---|---|---|---|---|
| | Polymerizable monomer (A) | | | | | |
| Ex. No. | Phosphoric acid-type monomer (A1) | Non-acidic monomer (A2) | Earth metal ion source (B) | Organic solvent | Water | Polymerization initiator |
| 1 | PM(15) | BisGMA(30), 3G(20), HEMA(35) | Al(O-i-Pr)$_3$(4.0) | IPA(85) | water(15) | CQ(1.0), DMBE(1.5) |
| 2 | PM(25) | BisGMA(30), 3G(20), HEMA(25) | Al(O-i-Pr)$_3$(3.5) | IPA(85) | water(15) | CQ(1.0), DMBE(1.5) |
| 3 | PM(25) | BisGMA(30), 3G(20), HEMA(25) | Al(O-i-Pr)$_3$(7.0) | IPA(85) | water(15) | CQ(1.0), DMBE(1.5) |
| 4 | PM(25) | BisGMA(30), 3G(20), HEMA(25) | Al(O-i-Pr)$_3$(9.0) | IPA(85) | water(15) | CQ(1.0), DMBE(1.5) |
| 5 | PM(25) | BisGMA(30), HEMA(25) MAC-10(20) | Al(O-i-Pr)$_3$(15.0) | IPA(85) | water(15) | CQ(1.0), DMBE(1.5) |
| 6 | PM(25) | BisGMA(30), 3G(20), HEMA(25) | Al(OH)$_3$(2.6) | IPA(85) | water(15) | CQ(1.0), DMBE(1.5) |
| 7 | PM(25) | BisGMA(30), 3G(20), HEMA(25) | La(O-i-Pr)$_3$(10.0) | IPA(85) | water(15) | CQ(1.0), DMBE(1.5) |
| 8 | PM(25) | BisGMA(30), 3G(20), HEMA(25) | La(OH)$_3$(6.4) | IPA(85) | water(15) | CQ(1.0), DMBE(1.5) |
| 9 | PM(25) | BisGMA(30), 3G(20), HEMA(25) | Sc(O-i-Pr)$_3$(7.5) | IPA(85) | water(15) | CQ(1.0), DMBE(1.5) |
| 10 | PM(25) | BisGMA(30), 3G(20), HEMA(25) | Yb(O-i-Pr)$_3$(11.8) | IPA(85) | water(15) | CQ(1.0), DMBE(1.5) |
| 11 | PM(25) | BisGMA(30), 3G(20), HEMA(25) | MF(2) | IPA(85) | water(15) | CQ(1.0), DMBE(1.5) |
| 12 | PM(25) | BisGMA(30), 3G(20), HEMA(25) | MF(10) | IPA(85) | water(15) | CQ(1.0), DMBE(1.5) |
| 13 | PM(25) | BisGMA(30), 3G(20), HEMA(25) | MF(20) | IPA(85) | water(15) | CQ(1.0), DMBE(1.5) |
| 14 | PM(25) | BisGMA(30), 3G(20), HEMA(25) | MF(10) | IPA(85) | water(15) | TPO(1.0) |
| 15 | PM(25) | BisGMA(30), 3G(20), HEMA(25) | MF(10) | IPA(85) | water(15) | BTPO(1.0) |
| 16 | PM(25) | BisGMA(30), 3G(20), HEMA(25) | MF(10) | IPA(85) | water(15) | CQ(1.0), DMBE(1.5), TPO(1.0) |
| 17 | MDP(25) | BisGMA(30), 3G(20), HEMA(25) | MF(10) | IPA(85) | water(15) | CQ(1.0), DMBE(1.5) |
| 18 | HP(25) | BisGMA(30), 3G(20), HEMA(25) | MF(10) | IPA(85) | water(15) | CQ(1.0), DMBE(1.5) |
| 19 | PM(25) | BisGMA(25), HEMA(50) | MF(10) | IPA(85) | water(50) | CQ(1.0), DMBE(1.5) |
| 20 | PM(25) | BisGMA(25), HEMA(50) | MF(10) | — | water(15) | CQ(1.0), DMBE(1.5) |
| 21 | PM(25) | BisGMA(30), 3G(20), HEMA(25) | MF(10) | IPA(100) | — | CQ(1.0), DMBE(1.5) |

[1]Contains 0.03 parts by mass of BHT.

TABLE 2

| | Mol number (mmols/g) per g of polymerizable monomer | | | | |
|---|---|---|---|---|---|
| Ex. No. | Phosphoric acid-type monomer (A) | Other acidic monomer | Earth metal ion (B) | Other metal ion | Anion |
| 1 | PM1(0.42), PM2(0.18) | — | Al$^{3+}$(0.19) | — | — |
| 2 | PM1(0.71), PM2(0.28) | — | Al$^{3+}$(0.16) | — | — |
| 3 | PM1(0.72), PM2(0.29) | — | Al$^{3+}$(0.33) | — | — |
| 4 | PM1(0.71), PM2(0.27) | — | Al$^{3+}$(0.43) | — | — |
| 5 | PM1(0.72), PM2(0.27) | MAC-10 (0.60) | Al$^{3+}$(0.72) | — | — |
| 6 | PM1(0.71), PM2(0.27) | — | Al$^{3+}$(0.32) | — | — |
| 7 | PM1(0.72), PM2(0.28) | — | La$^{3+}$(0.31) | — | — |
| 8 | PM1(0.72), PM2(0.29) | — | La$^{3+}$(0.32) | — | — |
| 9 | PM1(0.72), PM2(0.28) | — | Sc$^{3+}$(0.32) | — | — |
| 10 | PM1(0.72), PM2(0.27) | — | Yb$^{3+}$(0.31) | — | — |
| 11 | PM1(0.70), PM2(0.27) | — | Al$^{3+}$(0.12), La$^{3+}$(0.05) | Ca$^{2+}$(0.01) | F$^-$(0.3) |
| 12 | PM1(0.71), PM2(0.27) | — | Al$^{3+}$(0.58), La$^{3+}$(0.23) | Ca$^{2+}$(0.07) | F$^-$(1.6) |
| 13 | PM1(0.71), PM2(0.27) | — | Al$^{3+}$(1.14), La$^{3+}$(0.25) | Ca$^{2+}$(0.12) | F$^-$(3.0) |

TABLE 2-continued

| | | | | Durability of adhesion dhesion test A/MPa (standard deviation) | |
|---|---|---|---|---|---|
| Ex. No. | $R_E$ | $R_T$ | pH | Enamel | Dentin |
| 1 | 0.56 | 0.56 | 2.0 | 17.5(1.9) | 13.1(1.8) |
| 2 | 0.28 | 0.28 | 1.7 | 16.7(2.9) | 12.2(3.8) |
| 3 | 0.57 | 0.57 | 2.1 | 18.1(3.9) | 14.2(2.8) |
| 4 | 0.76 | 0.76 | 3.1 | 19.3(3.4) | 15.2(2.1) |
| 5 | 1.26 | 1.26 | 2.6 | 15.2(3.3) | 12.2(2.9) |
| 6 | 0.57 | 0.57 | 2.2 | 18.5(2.9) | 14.4(2.1) |
| 7 | 0.54 | 0.54 | 2.1 | 20.3(2.2) | 17.2(3.5) |
| 8 | 0.55 | 0.55 | 2.1 | 20.9(3.2) | 17.8(3.1) |
| 9 | 0.56 | 0.56 | 2.2 | 15.2(1.2) | 13.8(2.5) |
| 10 | 0.54 | 0.54 | 2.2 | 15.2(1.8) | 12.0(2.2) |
| 11 | 0.31 | 0.32 | 2.0 | 19.4(2.1) | 14.2(2.3) |
| 12 | 1.44 | 1.52 | 2.4 | 20.1(2.9) | 16.2(3.1) |
| 13 | 2.47 | 2.61 | 3.7 | 19.6(2.5) | 13.1(2.5) |

| | Mol number (mmols/g) per g of polymerizable monomer | | | | |
|---|---|---|---|---|---|
| Ex. No. | Phosphoric acid-type monomer (A) | Other acidic monomer | Earth metal ion (B) | Other metal ion | Anion |
| 14 | PM1(0.70), PM2(0.27) | — | $Al^{3+}$(0.57), $La^{3+}$(0.23) | $Ca^{2+}$(0.06) | $F^-$(1.5) |
| 15 | PM1(0.71), PM2(0.28) | — | $Al^{3+}$(0.56), $La^{3+}$(0.22) | $Ca^{2+}$(0.07) | $F^-$(1.5) |
| 16 | PM1(0.70), PM2(0.28) | — | $Al^{3+}$(0.58), $La^{3+}$(0.23) | $Ca^{2+}$(0.07) | $F^-$(1.6) |
| 17 | MDP(0.78) | — | $Al^{3+}$(0.58), $La^{3+}$(0.24) | $Ca^{2+}$(0.06) | $F^-$(1.6) |
| 18 | HP(0.80) | — | $Al^{3+}$(0.58), $La^{3+}$(0.22) | $Ca^{2+}$(0.06) | $F^-$(1.6) |
| 19 | PM1(0.71), PM2(0.28) | — | $Al^{3+}$(0.58), $La^{3+}$(0.24) | $Ca^{2+}$(0.06) | $F^-$(1.6) |
| 20 | PM1(0.69), PM2(0.23) | — | $Al^{3+}$(0.55), $La^{3+}$(0.19) | $Ca^{2+}$(0.03) | $F^-$(1.1) |
| 21 | PM1(0.63), PM2(0.12) | — | $Al^{3+}$(0.50), $La^{3+}$(0.13) | $Ca^{2+}$(0.02) | $F^-$(0.9) |

| | | | | Durability of adhesion dhesion test A/MPa (standard deviation) | |
|---|---|---|---|---|---|
| Ex. No. | $R_E$ | $R_T$ | pH | Enamel | Dentin |
| 14 | 1.44 | 1.51 | 2.1 | 21.1(2.8) | 17.0(3.1) |
| 15 | 1.38 | 1.46 | 2.1 | 20.9(1.8) | 17.2(3.3) |
| 16 | 1.45 | 1.53 | 2.3 | 20.1(2.9) | 17.5(3.1) |
| 17 | 1.57 | 1.65 | 2.0 | 21.0(4.1) | 15.4(3.1) |
| 18 | 1.50 | 1.57 | 2.1 | 18.0(2.8) | 14.2(3.4) |
| 19 | 1.45 | 1.52 | 2.1 | 20.1(2.5) | 16.0(2.1) |
| 20 | 1.38 | 1.42 | 1.9 | 15.0(3.3) | 12.1(3.2) |
| 21 | 1.37 | 1.40 | 2.0 | 13.0(2.4) | 10.1(4.2) |

$R_E$: Total valency ratio of the earth metal ions to the phosphoric acid-type monomer (A1).
$R_T$: Total valency ratio of metal ions other than the earth metal ions to the total metal ions.

TABLE 3

| | Adhesive for composite resin (mass parts)[1] | | | | | |
|---|---|---|---|---|---|---|
| | Polymerizable monomer (A) | | | | | |
| Comp. Ex. No. | Phosphoric acid-type monomer (A1) | Non-acidic monomer (A2) | Metal ion source (B) | Organic solvent | Water | Polymerization initiator |
| 1 | PM(25) | BisGMA(30), 3G(20), HEMA(25) | — | IPA(85) | water(15) | CQ(1.0), DMBE(1.5) |
| 2 | MDP(25) | BisGMA(30), 3G(20), HEMA(25) | — | IPA(85) | water(15) | CQ(1.0), DMBE(1.5) |
| 3 | HP(25) | BisGMA(30), 3G(20), HEMA(25) | — | IPA(85) | water(15) | CQ(1.0), DMBE(1.5) |
| 4 | PM(25) | BisGMA(25), HEMA(50) | — | — | water(15) | CQ(1.0), DMBE(1.5) |
| 5 | PM(25) | BisGMA(30), 3G(20), HEMA(25) | — | IPA(85) | — | CQ(1.0), DMBE(1.5) |

TABLE 3-continued

Adhesive for composite resin (mass parts)[1]

| Comp. Ex. No. | Polymerizable monomer (A) Phosphoric acid-type monomer (A1) | Non-acidic monomer (A2) | Metal ion source (B) | Organic solvent | Water | Polymerization initiator |
|---|---|---|---|---|---|---|
| 6 | PM(25) | BisGMA(30), 3G(20), HEMA(25) | $Mg(OH)_2$(2.9) | IPA(85) | water(15) | CQ(1.0), DMBE(1.5) |
| 7 | PM(25) | BisGMA(30), 3G(20), HEMA(25) | $Ca(OH)_2$(3.7) | IPA(85) | water(15) | CQ(1.0), DMBE(1.5) |
| 8 | PM(25) | BisGMA(30), 3G(20), HEMA(25) | $Ba(OH)_2$(8.6) | IPA(85) | water(15) | CQ(1.0), DMBE(1.5) |
| 9 | PM(25) | BisGMA(30), 3G(20), HEMA(25) | $Ti(O-i-Pr)_4$(7.1) | IPA(85) | water(15) | CQ(1.0), DMBE(1.5) |
| 10 | PM(25) | BisGMA(30), 3G(20), HEMA(25) | $Zr(O-i-Pr)_4$(8.2) | IPA(85) | water(15) | CQ(1.0), DMBE(1.5) |
| 11 | PM(25) | BisGMA(30), 3G(20), HEMA(25) | $V(acac)_3$(11.6) | IPA(85) | water(15) | CQ(1.0), DMBE(1.5) |
| 12 | PM(25) | BisGMA(30), 3G(20), HEMA(25) | $Cr(O-i-Pr)_3$(7.6) | IPA(85) | water(15) | CQ(1.0), DMBE(1.5) |
| 13 | PM(25) | BisGMA(30), 3G(20), HEMA(25) | $Mn(acac)_3$(11.7) | IPA(85) | water(15) | CQ(1.0), DMBE(1.5) |
| 14 | PM(25) | BisGMA(30), 3G(20), HEMA(25) | $Fe(OEt)_3$(6.4) | IPA(85) | water(15) | CQ(1.0), DMBE(1.5) |
| 15 | PM(25) | BisGMA(30), 3G(20), HEMA(25) | $Co(acac)_3$(11.8) | IPA(85) | water(15) | CQ(1.0), DMBE(1.5) |
| 16 | PM(25) | BisGMA(30), 3G(20), HEMA(25) | $Ni(acac)_2$(12.8) | IPA(85) | water(15) | CQ(1.0), DMBE(1.5) |
| 17 | PM(25) | BisGMA(30), 3G(20), HEMA(25) | $Cu(OEt)_2$(7.7) | IPA(85) | water(15) | CQ(1.0), DMBE(1.5) |
| 18 | PM(25) | BisGMA(30), 3G(20) HEMA(25) | $Zn(OCH_2CH_2OMe)_2$ (10.7) | IPA(85) | water(15) | CQ(1.0), DMBE(1.5) |
| 19 | PM(25) | BisGMA(30), 3G(20), HEMA(25) | $Al_2O_3$(7.0) | IPA(85) | water(15) | CQ(1.0), DMBE(1.5) |
| 20 | PM(25) | BisGMA(30), 3G(20), HEMA(25) | $Al(sal)_3$(14.0) | IPA(85) | water(15) | CQ(1.0), DMBE(1.5) |
| 21 | PM(25) | BisGMA(30), 3G(20), HEMA(25) | $AlCl_3$(4.4) | IPA(85) | water(15) | CQ(1.0), DMBE(1.5) |
| 22 | PM(25) | BisGMA(30), 3G(20), HEMA(25) | $Al(O-i-Pr)_3$(1.0) | IPA(85) | water(15) | CQ(1.0), DMBE(1.5) |
| 23 | PM(25) | BisGMA(30), 3G(20), HEMA(25) | $Al(O-i-Pr)_3$(15.0) | IPA(85) | water(15) | CQ(1.0), DMBE(1.5) |
| 24 | PM(25) | BisGMA(30), 3G(20), HEMA(25) | MF(1.0) | IPA(85) | water(15) | CQ(1.0), DMBE(1.5) |
| 25 | PM(25) | BisGMA(30), 3G(20), HEMA(25) | MF(30.0) | IPA(85) | water(15) | CQ(1.0), DMBE(1.5) |
| 26 | — | BisGMA(30), 3G(20), HEMA(25) MAC-10(25) | MF(10) | IPA(85) | water(15) | CQ(1.0), DMBE(1.5) |
| 27[2] | PM(25) | BisGMA(30), 3G(20), HEMA(25) | MF(10) | IPA(85) | water(15) | CQ(1.0), DMBE(1.5) |

[1]Contains 0.03 parts by mass of BHT.
[2]An adhesion test piece was prepared by effecting the stirring for one hour to measure the ion concentrations and pH.

TABLE 4

| Comp. Ex. No. | Mol number (mmols/g) per g of polymerizable monomer | | | | |
|---|---|---|---|---|---|
| | Phosphoric acid-type monomer (A) | Other acidic monomer | Earth metal ion (B) | Other metal ion | Anion |
| 1 | PM1(0.71), PM2(0.27) | — | — | — | — |
| 2 | MDP(0.78) | — | — | — | — |
| 3 | HP(0.80) | — | — | — | — |
| 4 | PM1(0.71), PM2(0.27) | — | — | — | — |
| 5 | PM1(0.71), PM2(0.27) | — | — | — | — |
| 6 | PM1(0.72), PM2(0.28) | — | — | $Mg^{2+}$(0.49) | — |
| 7 | PM1(0.72), PM2(0.27) | — | — | $Ca^{2+}$(0.49) | — |
| 8 | PM1(0.73), PM2(0.28) | — | — | $Ba^{2+}$(0.48) | — |
| 9 | PM1(0.71), PM2(0.26) | — | — | $Ti^{4+}$(0.10) | — |
| 10 | PM1(0.71), PM2(0.26) | — | — | $Zr^{4+}$(0.09) | — |
| 11 | PM1(0.71), PM2(0.27) | — | — | $V^{3+}$(0.30) | — |
| 12 | PM1(0.71), PM2(0.28) | — | — | $Cr^{3+}$(0.31) | — |
| 13 | PM1(0.72), PM2(0.27) | — | — | $Mn^{2+}$(0.45) | — |

TABLE 4-continued

| | | | | | |
|---|---|---|---|---|---|
| 14 | PM1(0.71), PM2(0.26) | — | — | $Fe^{3+}(0.31)$ | — |
| 15 | PM1(0.72), PM2(0.27) | — | — | $Co^{3+}(0.30)$ | — |
| 16 | PM1(0.71), PM2(0.29) | — | — | $Ni^{2+}(0.47)$ | — |
| 17 | PM1(0.70), PM2(0.27) | — | — | $Cu^{2+}(0.48)$ | — |
| 18 | PM1(0.71), PM2(0.29) | — | — | $Zn^{2+}(0.45)$ | — |

| Comp. Ex. No. | $R_E$ | $R_T$ | pH | Durability of adhesion Adhesion test A/MPa (standard deviation) | |
|---|---|---|---|---|---|
| | | | | Enamel | Dentin |
| 1 | — | — | 1.0 | 4.1(3.2) | 5.3(2.8) |
| 2 | — | — | 1.1 | 8.8(3.1) | 5.1(3.1) |
| 3 | — | — | 1.1 | 3.1(4.1) | 4.4(4.2) |
| 4 | — | — | 1.1 | 2.0(1.1) | 2.4(1.1) |
| 5 | — | — | 1.2 | 3.1(4.1) | 5.4(4.1) |
| 6 | — | 0.57 | 2.2 | 12.4(1.2) | 9.3(3.4) |
| 7 | — | 0.57 | 2.2 | 11.8(3.5) | 8.2(1.3) |
| 8 | — | 0.55 | 2.1 | 12.4(4.0) | 8.3(2.5) |
| 9 | — | 0.24 | 1.2 | 14.1(5.3) | 9.8(1.9) |
| 10 | — | 0.02 | 1.2 | 13.5(1.2) | 8.7(3.2) |
| 11 | — | 0.53 | 2.1 | 10.2(4.1) | 6.8(1.8) |
| 12 | — | 0.55 | 2.0 | 9.3(2.9) | 6.1(3.1) |
| 13 | — | 0.53 | 2.1 | 8.9(3.5) | 6.2(4.3) |
| 14 | — | 0.55 | 2.2 | 14.3(1.2) | 9.1(1.1) |
| 15 | — | 0.53 | 2.0 | 9.1(3.3) | 5.6(3.2) |
| 16 | — | 0.55 | 2.0 | 9.3(2.2) | 7.3(2.6) |
| 17 | — | 0.57 | 1.9 | 8.1(3.2) | 5.4(2.8) |
| 18 | — | 0.53 | 2.0 | 10.8(3.1) | 8.1(3.1) |

| Comp. Ex. No. | Mol number (mmols/g) per g of polymerizable monomer | | | | |
|---|---|---|---|---|---|
| | Phosphoric acid-type monomer (A) | Other acidic monomer | Earth metal ion (B) | Other metal ion | Anion |
| 19 | PM1(0.70), PM2(0.27) | — | $Al^{3+}(0.01)$ | — | — |
| 20 | PM1(0.72), PM2(0.28) | — | $Al^{3+}(0.07)$ | — | — |
| 21 | PM1(0.73), PM2(0.22) | — | $Al^{3+}(0.27)$ | — | $Cl^-(0.82)$ |
| 22 | PM1(0.72), PM2(0.27) | — | $Al^{3+}(0.05)$ | — | — |
| 23 | PM1(0.72), PM2(0.28) | — | $Al^{3+}(0.71)$ | — | — |
| 24 | PM1(0.71), PM2(0.26) | — | $Al^{3+}(0.05)$, $La^{3+}(0.01)$ | $Ca^{2+}(0.01)$ | $F^-(0.2)$ |
| 25 | PM1(0.73), PM2(0.27) | — | $Al^{3+}(1.68)$, $La^{3+}(0.65)$ | $Ca^{2+}(0.22)$ | $F^-(4.4)$ |
| 26 | — | MAC-10 (0.83) | $Al^{3+}(0.51)$, $La^{3+}(0.13)$ | $Ca^{2+}(0.07)$ | $F^-(1.1)$ |
| 27[1] | PM1(0.72), PM2(0.28) | — | $Al^{3+}(0.06)$, $La^{3+}(0.01)$ | $Ca^{2+}(0.07)$ | $F^-(0.1)$ |

| Comp. Ex. No. | $R_E$ | $R_T$ | pH | Durability of adhesion Adhesion test A/MPa (standard deviation) | |
|---|---|---|---|---|---|
| | | | | Enamel | Dentin |
| 19 | 0.02 | — | 1.2 | 11.1(4.3) | 7.4(4.6) |
| 20 | 0.12 | — | 1.3 | 10.9(2.3) | 7.7(2.6) |
| 21 | 0.48 | — | 1.2 | 6.1(3.2) | 4.3(2.6) |
| 22 | 0.09 | — | 1.3 | 12.4(2.2) | 8.9(3.3) |
| 23 | 1.24 | — | 5.8 | 8.8(4.5) | 4.2(3.5) |
| 24 | 0.11 | 0.12 | 1.4 | 12.8(3.5) | 9.2(1.3) |
| 25 | 4.00 | 4.30 | 5.2 | 8.4(4.0) | 5.3(2.5) |
| 26 | 1.15[2] | 1.24[2] | 3.3 | 3.5(2.0) | 9.1(2.5) |
| 27[1] | 0.12 | 0.20 | 1.8 | 10.4(3.5) | 7.1(2.2) |

[1] An adhesion test piece was prepared by effecting the stirring for one hour to measure the ion concentrations and pH.
[2] Total ionic valency of earth metal ions/total valency of MAC-10.

The compositions of Examples 1 to 21 are so constituted that the total valency ratio ($R_E$) of the earth metal ions to the phosphoric acid-type monomer satisfies the range specified by the present invention and, therefore, feature very high durability of adhesion to either the enamel or the dentin.

On the other hand, the compositions of Comparative Examples 1 to 18 do not quite contain metal ions, or contain metal ions but without earth metal ions and, therefore, exhibit low adhesive strength to either the dentin or the enamel in the test of durability.

In Comparative Example 19, aluminum oxide is used as the earth metal ion source (B). Therefore, Al ions (earth metal ions) are not almost eluted out, and the adhesive strength to the dentin, in particular, is considerably low.

In Comparative Example 20, aluminum salicylate is used as the earth metal ion source. Therefore, Al ions (earth metal ions) are not almost eluted out, and the adhesive strength to the dentin, in particular, is considerably low.

In Comparative Example 21, aluminum chloride is used as the earth metal ion source. Though Al ions elute out, chloride ions (pKa of hydrogen chloride is −6.1) which are conjugated base ions more strongly acidic than phosphoric acid contained therein make it difficult to obtain good adhesive strength to the dentin, in particular.

In Comparative Examples 22 to 25, though the earth metal ions are present, the total valency ratios ($R_E$) lie outside the range of the invention or the compositions fail to exhibit acidic property. Therefore, the adhesive strengths are low to either the dentin or the enamel.

In Comparative Example 26, use is made of an acidic group-containing polymer other than the phosphoric acid-type monomer. Therefore, good adhesiveness, particularly, to the enamel is not obtained.

Comparative Example 27 uses the fluoroaluminosilicate glass as the earth metal ion source (B), and its composition has been so adjusted that the amount of the earth metal ions therein lies in the range of the present invention. However, since the stirring time (ripening time) is as short as one hour, the earth metal ions elute out only little. As a result, the adhesive strength, particularly, to the dentin is low.

Examples 22 to 29, Comparative Examples 28 to 33

Adhesive compositions (pretreating agents) were prepared in the same manner as in Example 1 by using the components according to the compositions shown in Table 5 or 7. The compositions were measured and evaluated for their adhesive strengths to the enamel and the dentin. The results were as shown in Table 6 and Table 8.

TABLE 5

| | Pre-treating agent (mass parts)[1] | | | | |
|---|---|---|---|---|---|
| | Polymerizable monomer (A) | | | | |
| Ex. No. | Phosphoric acid-type monomer (A1) | Non-acidic monomer (A2) | Earth metal ion source (B) | Organic solvent | Water |
| 22 | PM(20) | HEMA(80) | Al(O-i-Pr)$_3$(5.0) | IPA(85) | water(20) |
| 23 | PM(50) | HEMA(50) | Al(O-i-Pr)$_3$(12.0) | IPA(85) | water(20) |
| 24 | PM(50) | HEMA(50) | La(O-i-Pr)$_3$(18.6) | IPA(85) | water(20) |
| 25 | PM(50) | HEMA(50) | MF(5) | IPA(85) | water(20) |
| 26 | PM(50) | HEMA(50) | MF(15) | IPA(85) | water(20) |
| 27 | PM(50) | HEMA(50) | MF(15) | IPA(85) | water(80) |
| 28 | PM(20) | HEMA(80) | MF(15) | IPA(100) | water(20) |
| 29 | PM(50) | HEMA(45), Bis-GMA(5) | MF(15) | IPA(85) | water(20) |

[1] Contains 0.03 parts by mass of BHT.

TABLE 6

| | Mol number (mmols/g) per g of polymerizable monomer | | | |
|---|---|---|---|---|
| Ex. No. | Phosphoric acid-type monomer (A1) | Earth metal ion (B) | Other metal ion | Anion |
| 22 | PM1(0.56), PM2(0.24) | Al$^{3+}$(0.24) | | — |
| 23 | PM1(1.38), PM2(0.57) | Al$^{3+}$(0.57) | | — |
| 24 | PM1(1.37), PM2(0.57) | La$^{3+}$(0.58) | | — |
| 25 | PM1(1.37), PM2(0.57) | Al$^{3+}$(0.29), La$^{3+}$(0.11) | Ca$^{2+}$(0.03) | F$^-$(0.75) |
| 26 | PM1(1.38), PM2(0.58) | Al$^{3+}$(0.86), La$^{3+}$(0.33) | Ca$^{2+}$(0.09) | F$^-$(2.3) |
| 27 | PM1(1.38), PM2(0.58) | Al$^{3+}$(0.87), La$^{3+}$(0.34) | Ca$^{2+}$(0.09) | F$^-$(2.4) |
| 28 | PM1(0.57), PM2(0.24) | Al$^{3+}$(0.85), La$^{3+}$(0.32) | Ca$^{2+}$(0.09) | F$^-$(2.32) |
| 29 | PM1(1.39), PM2(0.58) | Al$^{3+}$(0.84), La$^{3+}$(0.33) | Ca$^{2+}$(0.09) | F$^-$(2.30) |

| Ex. No. | $R_E$ | $R_T$ | pH | Durability of adhesion Adhesion test A/MPa (standard deviation) | |
|---|---|---|---|---|---|
| | | | | Enamel | Dentin |
| 22 | 0.53 | — | 2.1 | 16.8(2.2) | 14.3(2.1) |
| 23 | 0.51 | — | 2.2 | 17.3(3.1) | 15.7(4.1) |
| 24 | 0.52 | — | 2.2 | 18.1(2.5) | 16.3(1.3) |
| 25 | 0.36 | 0.38 | 1.6 | 18.4(1.8) | 16.8(2.4) |
| 26 | 1.07 | 1.12 | 2.3 | 19.1(5.3) | 16.8(1.9) |
| 27 | 1.09 | 1.14 | 2.3 | 19.5(4.3) | 17.1(2.4) |
| 28 | 2.54 | 2.67 | 3.8 | 17.1(2.3) | 13.8(2.1) |
| 29 | 1.04 | 1.09 | 2.1 | 16.1(5.3) | 14.1(2.1) |

TABLE 7

| | Pre-treating agent (mass parts)[1] | | | | |
|---|---|---|---|---|---|
| | Polymerizable monomer (A) | | | | |
| Comp. Ex. No. | Phosphoric acid-type monomer (A1) | Non-acidic monomer (A2) | Metal ion source (B) | Organic solvent | Water |
| 28 | PM(50) | HEMA(50) | — | IPA(85) | water(20) |
| 29 | PM(50) | HEMA(50) | $Ca(OH)_2$(6.6) | IPA(85) | water(20) |
| 30 | PM(50) | HEMA(50) | $Ti(O-i-Pr)_4$(12.8) | IPA(85) | water(20) |
| 31 | PM(50) | HEMA(50) | $Fe(OEt)_3$(11.4) | IPA(85) | water(20) |
| 32 | PM(50) | HEMA(50) | MF(2.0) | IPA(85) | water(20) |
| 33 | PM(20) | HEMA(80) | MF(25) | IPA(85) | water(20) |

[1])Contains 0.03 parts by mass of BHT.

TABLE 8

| Comp. Ex. No. | Mol number (mmols/g) per g of polymerizable monomer | | | |
|---|---|---|---|---|
| | Phosphoric acid-type monomer (A1) | Earth metal ion (B) | Other metal ion | Anion |
| 28 | PM1(1.38), PM2(0.58) | — | — | — |
| 29 | PM1(1.39), PM2(0.57) | — | $Ca^{2+}$(0.88) | — |
| 30 | PM1(1.37), PM2(0.55) | — | $Ti^{4+}$(0.19) | — |
| 31 | PM1(1.38), PM2(0.56) | — | $Fe^{3+}$(0.58) | — |
| 32 | PM1(1.36), PM2(0.57) | $Al^{3+}$(0.11), $La^{3+}$(0.04) | $Ca^{2+}$(0.01) | $F^-$(0.03) |
| 33 | PM1(0.56), PM2(0.24) | $Al^{3+}$(1.41), $La^{3+}$(0.54) | $Ca^{2+}$(0.15) | $F^-$(3.6) |

| Comp. Ex. No. | | | | Durability of adhesion Adhesion test A/MPa (standard deviation) | |
|---|---|---|---|---|---|
| | $R_E$ | $R_T$ | pH | Enamel | Dentin |
| 28 | — | — | 1.2 | 7.1(3.2) | 5.3(2.8) |
| 29 | — | 0.52 | 2.1 | 11.3(3.1) | 5.5(3.1) |
| 30 | — | 0.23 | 1.3 | 12.1(4.1) | 8.7(4.1) |
| 31 | — | 0.52 | 2.0 | 13.3(1.2) | 9.1(3.4) |
| 32 | 0.136 | 0.14 | 1.3 | 13.2(3.5) | 9.3(1.3) |
| 33 | 4.30 | 4.52 | 5.5 | 9.3(4.0) | 6.3(2.5) |

In Examples 22 to 29, the components are so blended as to satisfy the constitution contemplated by the present invention, and favorable durability of adhesion is attained to both the enamel and the dentin.

In Comparative Examples 28 to 33, the earth metal ions are not contained or are contained but in such amounts that the total valency ratios ($R_E$) thereof lie outside the range of the invention. Therefore, good adhesive strength is not obtained, particularly, to the dentin.

Experimental Example II

Experiment 1

A dental adhesive composition (adhesive for composite resin) was prepared in quite the same manner as in Example 1 but further adding 0.7 g of FS2 as the fumed silica.

The above composition was measured concerning pH, phosphoric acid-type monomer, metal ions and anions in the same manner as in Example 1. Further, a test piece I for evaluating the adhesive was prepared and was evaluated for its durability of adhesion to the enamel and the dentin according to the adhesion test B.

Monomer composition in the above composition is shown in Table 9, blended components other than the polymerizable monomer are shown in Table 10, and the amount of the phosphoric acid-type monomer and the amount of the earth metal ions are shown in Table 11. Further, Table 12 shows the total valency ratio ($R_E$) of the earth metal ions to the phosphoric acid-type monomer, pH of the composition and the tested results of the durability of adhesion.

Experiments 2 to 24

Dental adhesive compositions (adhesives for composite resin) were prepared in the same manner as in Experiment 1 but varying the kinds and blending amounts of the fumed silica, and varying the blended compositions of other components, and were measured and evaluated for their durability of adhesion according to the adhesion test B.

The monomer compositions in the obtained compositions are shown in Table 9, blended compositions of the components other than the polymerizable monomers are shown in Table 10, amounts of the phosphoric acid-type monomers and the amounts of the earth metal ions are shown in Table 11, and the total valency ratios ($R_E$) of the earth metal ions to the phosphoric acid-type monomers, pH of the compositions and the tested results of the durability of adhesion are shown in Table 12.

Comparative Experiments 1 to 8

Dental adhesive compositions (adhesives for composite resin) were prepared in the same manner as in Experiment 1 but using other inorganic fillers instead of the fumed silica and varying the blended composition, and were measured and evaluated for their durability of adhesion according to the adhesion test B.

The monomer compositions in the obtained compositions are shown in Table 13, blended compositions of the components other than the polymerizable monomers are shown in Table 14, amounts of the phosphoric acid-type monomers and the amounts of the earth metal ions are shown in Table 15, and the total valency ratios ($R_E$) of the earth metal ions to the phosphoric acid-type monomers, pH of the compositions and the tested results of the durability of adhesion are shown in Table 16.

TABLE 9

| | Adhesive for composite resin (mass parts)[1] | |
|---|---|---|
| | Polymerizable monomer (A) | |
| Expt. No. | Phosphoric acid-type monomer (A1) | Non-acidic monomer (A2) |
| 1 | PM (15) | BisGMA (30), 3G (20), HEMA (35) |
| 2 | PM (25) | BisGMA (30), 3G (20), HEMA (25) |
| 3 | PM (25) | BisGMA (30), 3G (20), HEMA (25) |
| 4 | PM (25) | BisGMA (30), 3G (20), HEMA (25) |
| 5 | PM (25) | BisGMA (30), 3G (20), HEMA (25) |
| 6 | PM (25) | BisGMA (30), 3G (20), HEMA (25) |
| 7 | PM (25) | BisGMA (30), 3G (20), HEMA (25) |
| 8 | PM (25) | BisGMA (30), 3G (20), HEMA (25) |
| 9 | PM (25) | BisGMA (30), 3G (20), HEMA (25) |
| 10 | PM (25) | BisGMA (30), 3G (20), HEMA (25) |
| 11 | PM (25) | BisGMA (30), 3G (20), HEMA (25) |
| 12 | PM (25) | BisGMA (30), 3G (20), HEMA (25) |
| 13 | PM (25) | BisGMA (30), 3G (20), HEMA (25) |
| 14 | PM (25) | BisGMA (30), 3G (20), HEMA (25) |
| 15 | PM (25) | BisGMA (30), 3G (20), HEMA (25) |
| 16 | PM (25) | BisGMA (30), 3G (20), HEMA (25) |
| 17 | PM (25) | BisGMA (30), 3G (20), HEMA (25) |
| 18 | PM (25) | BisGMA (30), 3G (20), HEMA (25) |
| 19 | PM (25) | BisGMA (30), 3G (20), HEMA (25) |
| 20 | PM (25) | BisGMA (30), 3G (20), HEMA (25) |
| 21 | MDP (25) | BisGMA (30), 3G (20), HEMA (25) |
| 22 | HP (25) | BisGMA (30), 3G (20), HEMA (25) |
| 23 | PM (25) | BisGMA (25), HEMA (50) |
| 24 | PM (25) | BisGMA (25), HEMA (50) |

[1]Contains 0.03 parts by mass of BHT.

TABLE 10

| | Adhesive for composite resin (mass parts) | | | | |
|---|---|---|---|---|---|
| Expt. No. | Earth metal ion source (B) | Filler | Organic solvent | Water | Polymerization initiator |
| 1 | Al(O-i-Pr)$_3$(4.0) | FS2(7.0) | IPA(85) | water(15) | CQ(1.0), DMBE(1.5) |
| 2 | Al(O-i-Pr)$_3$(7.0) | FS2(2.0) | IPA(85) | water(15) | CQ(1.0), DMBE(1.5) |
| 3 | Al(O-i-Pr)$_3$(7.0) | FS2(7.0) | IPA(85) | water(15) | CQ(1.0), DMBE(1.5) |
| 4 | Al(O-i-Pr)$_3$(7.0) | FS2(14.0) | IPA(85) | water(15) | CQ(1.0), DMBE(1.5) |
| 5 | Al(O-i-Pr)$_3$(7.0) | FS1(7.0) | IPA(85) | water(15) | CQ(1.0), DMBE(1.5) |
| 6 | Al(O-i-Pr)$_3$(7.0) | FS3(7.0) | IPA(85) | water(15) | CQ(1.0), DMBE(1.5) |
| 7 | Al(O-i-Pr)$_3$(7.0) | FS4(7.0) | IPA(85) | water(15) | CQ(1.0), DMBE(1.5) |
| 8 | Al(O-i-Pr)$_3$(7.0) | FS5(7.0) | IPA(85) | water(15) | CQ(1.0), DMBE(1.5) |
| 9 | Al(O-i-Pr)$_3$(3.5) | FS2(7.0) | IPA(85) | water(15) | CQ(1.0), DMBE(1.5) |
| 10 | Al(O-i-Pr)$_3$(9.0) | FS2(7.0) | IPA(85) | water(15) | CQ(1.0), DMBE(1.5) |
| 11 | Al(OH)$_3$(2.6) | FS2(7.0) | IPA(85) | water(15) | CQ(1.0), DMBE(1.5) |
| 12 | La(O-i-Pr)$_3$(10.0) | FS2(7.0) | IPA(85) | water(15) | CQ(1.0), DMBE(1.5) |
| 13 | Sc(O-i-Pr)$_3$(7.5) | FS2(7.0) | IPA(85) | water(15) | CQ(1.0), DMBE(1.5) |
| 14 | Yb(O-i-Pr)$_3$(11.8) | FS2(7.0) | IPA(85) | water(15) | CQ(1.0), DMBE(1.5) |
| 15 | MF(2) | FS2(7.0) | IPA(85) | water(15) | CQ(1.0), DMBE(1.5) |
| 16 | MF(10) | FS2(7.0) | IPA(85) | water(15) | CQ(1.0), DMBE(1.5) |
| 17 | MF(20) | FS2(7.0) | IPA(85) | water(15) | CQ(1.0), DMBE(1.5) |
| 18 | MF(10) | FS2(7.0) | IPA(85) | water(15) | TPO(1.0) |
| 19 | MF(10) | FS2(7.0) | IPA(85) | water(15) | BTPO(1.0) |
| 20 | MF(10) | FS2(7.0) | IPA(85) | water(15) | CQ(1.0), DMBE(1.5), TPO(1.0) |
| 21 | MF(10) | FS2(7.0) | IPA(85) | water(15) | CQ(1.0), DMBE(1.5) |
| 22 | MF(10) | FS2(7.0) | IPA(85) | water(15) | CQ(1.0), DMBE(1.5) |
| 23 | MF(10) | FS2(7.0) | IPA(85) | water(50) | CQ(1.0), DMBE(1.5) |
| 24 | MF(10) | FS2(7.0) | — | water(15) | CQ(1.0), DMBE(1.5) |

TABLE 11

| | Mol number (mmols/g) per g of polymerizable monomer | | |
|---|---|---|---|
| Expt. No. | Phosphoric acid-type monomer (A1) | Earth metal ion (B) | Anion |
| 1 | PM1(0.42), PM2(0.18) | Al$^{3+}$(0.18) | — |
| 2 | PM1(0.71), PM2(0.28) | Al$^{3+}$(0.31) | — |
| 3 | PM1(0.72), PM2(0.29) | Al$^{3+}$(0.33) | — |
| 4 | PM1(0.71), PM2(0.27) | Al$^{3+}$(0.32) | — |
| 5 | PM1(0.72), PM2(0.27) | Al$^{3+}$(0.31) | — |
| 6 | PM1(0.72), PM2(0.27) | Al$^{3+}$(0.33) | — |
| 7 | PM1(0.72), PM2(0.26) | Al$^{3+}$(0.32) | — |
| 8 | PM1(0.71), PM2(0.26) | Al$^{3+}$(0.32) | — |
| 9 | PM1(0.71), PM2(0.28) | Al$^{3+}$(0.17) | — |
| 10 | PM1(0.72), PM2(0.27) | Al$^{3+}$(0.43) | — |
| 11 | PM1(0.71), PM2(0.27) | Al$^{3+}$(0.32) | — |
| 12 | PM1(0.72), PM2(0.28) | La$^{3+}$(0.30) | — |
| 13 | PM1(0.72), PM2(0.27) | Sc$^{3+}$(0.32) | — |
| 14 | PM1(0.72), PM2(0.27) | Yb$^{3+}$(0.30) | — |
| 15 | PM1(0.70), PM2(0.27) | Al$^{3+}$(0.12), La$^{3+}$(0.05), Ca$^{2+}$(0.01) | F$^-$(0.3) |
| 16 | PM1(0.71), PM2(0.27) | Al$^{3+}$(0.58), La$^{3+}$(0.23), Ca$^{2+}$(0.07) | F$^-$(1.6) |
| 17 | PM1(0.71), PM2(0.27) | Al$^{3+}$(1.14), La$^{3+}$(0.25), Ca$^{2+}$(0.12) | F$^-$(3.0) |
| 18 | PM1(0.70), PM2(0.27) | Al$^{3+}$(0.57), La$^{3+}$(0.23), Ca$^{2+}$(0.07) | F$^-$(1.5) |
| 19 | PM1(0.71), PM2(0.28) | Al$^{3+}$(0.56), La$^{3+}$(0.22), Ca$^{2+}$(0.06) | F$^-$(1.5) |
| 20 | PM1(0.70), PM2(0.28) | Al$^{3+}$(0.58), La$^{3+}$(0.23), Ca$^{2+}$(0.06) | F$^-$(1.6) |
| 21 | MDP(0.78) | Al$^{3+}$(0.58), La$^{3+}$(0.24), Ca$^{2+}$(0.06) | F$^-$(1.6) |

TABLE 11-continued

| | Mol number (mmols/g) per g of polymerizable monomer | | |
|---|---|---|---|
| Expt. No. | Phosphoric acid-type monomer (Al) | Earth metal ion (B) | Anion |
| 22 | HP(0.80) | $Al^{3+}$(0.58), $La^{3+}$(0.22), $Ca^{2+}$(0.06) | $F^-$(1.6) |
| 23 | PM1(0.72), PM2(0.28) | $Al^{3+}$(0.58), $La^{3+}$(0.24), $Ca^{2+}$(0.07) | $F^-$(1.6) |
| 24 | PM1(0.69), PM2(0.23) | $Al^{3+}$(0.55), $La^{3+}$(0.19), $Ca^{2+}$(0.03) | $F^-$(1.1) |

TABLE 12

| Expt. No. | $R_E$ | pH | Durability of adhesion Adhesion test B/MPa (standard deviation) | |
|---|---|---|---|---|
| | | | Enamel | Dentin |
| 1 | 0.53 | 2.0 | 16.1 (1.3) | 12.2 (2.5) |
| 2 | 0.55 | 1.7 | 15.3 (2.9) | 11.3 (3.8) |
| 3 | 0.57 | 2.1 | 16.9 (3.9) | 12.2 (2.8) |
| 4 | 0.57 | 2.1 | 17.3 (3.4) | 12.8 (2.1) |
| 5 | 0.54 | 2.1 | 15.2 (2.1) | 12.0 (1.1) |
| 6 | 0.58 | 2.2 | 17.2 (2.5) | 12.9 (3.2) |
| 7 | 0.56 | 2.1 | 15.8 (2.3) | 12.7 (2.5) |
| 8 | 0.57 | 2.1 | 14.2 (3.3) | 11.2 (2.3) |
| 9 | 0.30 | 1.8 | 15.2 (2.1) | 11.5 (4.3) |
| 10 | 0.75 | 3.2 | 15.9 (1.3) | 12.6 (2.4) |
| 11 | 0.57 | 2.3 | 16.6 (2.2) | 12.5 (2.1) |
| 12 | 0.52 | 2.1 | 18.3 (2.2) | 13.7 (3.5) |
| 13 | 0.56 | 2.2 | 15.3 (1.2) | 11.8 (3.5) |
| 14 | 0.53 | 2.2 | 15.5 (2.2) | 12.8 (2.8) |
| 15 | 0.31 | 2.0 | 19.4 (2.1) | 14.2 (2.3) |
| 16 | 1.44 | 2.4 | 19.1 (2.9) | 16.2 (3.1) |
| 17 | 2.47 | 3.7 | 17.6 (2.5) | 12.1 (2.5) |
| 18 | 1.44 | 2.1 | 19.1 (2.8) | 16.9 (3.1) |
| 19 | 1.38 | 2.1 | 20.9 (1.8) | 17.2 (3.3) |
| 20 | 1.45 | 2.3 | 20.1 (2.9) | 17.5 (3.1) |
| 21 | 1.58 | 2.0 | 21.0 (4.1) | 16.4 (3.1) |
| 22 | 1.50 | 2.1 | 17.0 (2.9) | 12.2 (3.4) |
| 23 | 1.43 | 2.3 | 19.8 (2.9) | 17.6 (2.1) |
| 24 | 1.38 | 1.9 | 18.9 (2.8) | 17.3 (1.3) |

TABLE 13

| | Adhesive for composite resin (mass parts)[1] Polymerizable monomer (A) | |
|---|---|---|
| Comp. Expt. No. | Phosphoric acid-type monomer (A1) | Non-acidic monomer (A2) |
| 1 | PM (25) | BisGMA (30), 3G (20), HEMA (25) |
| 2 | PM (25) | BisGMA (30), 3G (20), HEMA (25) |
| 3 | PM (25) | BisGMA (30), 3G (20), HEMA (25) |
| 4 | PM (25) | BisGMA (30), 3G (20), HEMA (25) |
| 5 | PM (25) | BisGMA (30), 3G (20), HEMA (25) |
| 6 | PM (25) | BisGMA (30), 3G (20), HEMA (25) |
| 7 | PM (25) | BisGMA (30), 3G (20), HEMA (25) |
| 8 | PM (25) | BisGMA (30), 3G (20), HEMA (25) |

[1]Contains 0.03 parts by mass of BHT.

TABLE 14

| Comp. Expt. No. | Adhesive for composite resin (mass parts) | | | | |
|---|---|---|---|---|---|
| | Earth metal ion source (B) | Inorganic filler | Organic solvent | Water | Polymerization initiator |
| 1 | Al(O-i-Pr)$_3$(7.0) | — | IPA(85) | water(15) | CQ(1.0), DMBE(1.5) |
| 2 | La(O-i-Pr)$_3$(10.0) | — | IPA(85) | water(15) | CQ(1.0), DMBE(1.5) |
| 3 | Sc(O-i-Pr)$_3$(7.5) | — | IPA(85) | water(15) | CQ(1.0), DMBE(1.5) |
| 4 | Yb(O-i-Pr)$_3$(11.8) | — | IPA(85) | water(15) | CQ(1.0), DMBE(1.5) |
| 5 | MF(10) | — | IPA(85) | water(15) | CQ(1.0), DMBE(1.5) |
| 6 | MF(10) | MS(7.0) | IPA(85) | water(15) | CQ(1.0), DMBE(1.5) |
| 7 | MF(10) | SS(7.0) | IPA(85) | water(15) | CQ(1.0), DMBE(1.5) |
| 8 | MF(10) | PS(7.0) | IPA(85) | water(15) | CQ(1.0), DMBE(1.5) |

TABLE 15

| Comp. Expt. No. | Mol number (mmols/g) per g of polymerizable monomer | | |
|---|---|---|---|
| | Phosphoric acid-type monomer (A1) | Earth metal ion (B) | Anion |
| 1 | PM1 (0.72), PM2 (0.26) | $Al^{3+}$ (0.33) | — |
| 2 | PM1 (0.72), PM2 (0.26) | $La^{3+}$ (0.31) | — |
| 3 | PM1 (0.72), PM2 (0.27) | $Sc^{3+}$ (0.32) | — |
| 4 | PM1 (0.72), PM2 (0.28) | $Yb^{3+}$ (0.31) | — |
| 5 | PM1 (0.70), PM2 (0.27) | $Al^{3+}$ (0.57), $La^{3+}$ (0.21), $Ca^{2+}$ (0.07) | $F^-$ (1.6) |
| 6 | PM1 (0.71), PM2 (0.27) | $Al^{3+}$ (0.57), $La^{3+}$ (0.22), $Ca^{2+}$ (0.07) | $F^-$ (1.6) |
| 7 | PM1 (0.73), PM2 (0.27) | $Al^{3+}$ (0.55), $La^{3+}$ (0.21), $Ca^{2+}$ (0.07) | $F^-$ (1.6) |
| 8 | PM1 (0.72), PM2 (0.27) | $Al^{3+}$ (0.58), $La^{3+}$ (0.23), $Ca^{2+}$ (0.06) | $F^-$ (1.6) |

TABLE 16

| Comp. Expt. No. | $R_E$ | pH | Durability of adhesion adhesion test B/MPa (standard deviation) | |
|---|---|---|---|---|
| | | | Enamel | Dentin |
| 1 | 0.58 | 2.1 | 9.2 (1.8) | 4.1 (2.5) |
| 2 | 0.55 | 2.2 | 10.1 (2.3) | 5.4 (3.29 |
| 3 | 0.56 | 2.1 | 8.3 (1.2) | 4.0 (2.1) |
| 4 | 0.54 | 2.1 | 8.0 (1.7) | 4.2 (3.3) |
| 5 | 1.40 | 2.2 | 11.5 (3.4) | 8.3 (2.1) |
| 6 | 1.40 | 2.3 | 11.5 (3.4) | 7.3 (2.1) |
| 7 | 1.32 | 2.2 | 12.2 (3.1) | 8.8 (1.1) |
| 8 | 1.42 | 2.4 | 5.2 (4.4) | 3.9 (3.1) |

As will be understood from the above experimental results, when the fumed silica is added, the durability of adhesion greatly increases as compared to when other inorganic filler is added, the adhesiveness greatly increases to either the enamel or the dentin, and the adhesive composition becomes very useful as an adhesive for composite resin.

Experiments 25 to 33, Comparative Experiments 9 to 11

Adhesive compositions for use as pretreating agents were prepared in the same manner as in Experiment 1 but in compliance with the blending compositions shown in Table 17.

The compositions were measured concerning pH, phosphoric acid-type monomer, metal ions and anions. Further, test pieces II for evaluating the pretreating agents were prepared and were tested for their durability of adhesion to the enamel and the dentin according to the adhesion test B.

The results of measurements and the tested results of the durability of adhesion were as shown in Table 18.

TABLE 17

| | Pre-treating agent (mass parts)[1] | | | | | |
|---|---|---|---|---|---|---|
| | Polymerizable monomer (A) | | | | | |
| Expt. No. | Phosphoric acid-type monomer (A1) | Non-acidic monomer (A2) | Earth metal ion source (B) | Inorganic filler | Organic solvent | Water |
| 25 | PM(20) | HEMA(80) | Al(O-i-Pr)$_3$(5.0) | FS2(7.0) | IPA(85) | water(20) |
| 26 | PM(50) | HEMA(50) | Al(O-i-Pr)$_3$(12.0) | FS2(7.0) | IPA(85) | water(20) |
| 27 | PM(50) | HEMA(50) | Al(O-i-Pr)$_3$(12.0) | FS2(2.0) | IPA(85) | water(20) |
| 28 | PM(50) | HEMA(50) | Al(O-i-Pr)$_3$(12.0) | FS2(14.0) | IPA(85) | water(20) |
| 29 | PM(50) | HEMA(50) | MF(5) | FS2(7.0) | IPA(85) | water(20) |
| 30 | PM(50) | HEMA(50) | MF(15) | FS2(7.0) | IPA(85) | water(20) |
| 31 | PM(50) | HEMA(50) | MF(15) | FS2(7.0) | IPA(85) | water(80) |
| 32 | PM(20) | HEMA(80) | MF(15) | FS2(7.0) | IPA(100) | water(20) |
| 33 | PM(50) | HEMA(45), Bis-GMA(5) | MF(15) | FS2(7.0) | IPA(85) | water(20) |
| *9 | PM(50) | HEMA(50) | Al(O-i-Pr)$_3$(12.0) | — | IPA(85) | water(20) |
| *10 | PM(50) | HEMA(50) | MF(15) | — | IPA(85) | water(20) |
| *11 | PM(50) | HEMA(50) | MF(15) | SS(7.0) | IPA(85) | water(20) |

[1]Contains 0.03 parts by mass of BHT.
*9 to 11 are Comparative Experiments.

TABLE 18

| Ex. No. | Mol number (mmols/g) per g of polymerizable monomer | | | Durability of adhesion Adhesion test B/MPa | | | |
|---|---|---|---|---|---|---|---|
| | Phosphoric acid-type monomer (A1) | Multivalent metal ion | Anion | $R_E$ | pH | (standard deviation) | |
| | | | | | | Enamel | Dentin |
| 25 | PM1(0.56), PM2(0.24) | $Al^{3+}$(0.24) | — | 0.53 | 2.1 | 15.8(2.2) | 13.3(2.1) |
| 26 | PM1(1.38), PM2(0.57) | $Al^{3+}$(0.57) | — | 0.51 | 2.2 | 17.3(3.1) | 15.7(4.1) |
| 27 | PM1(1.37), PM2(0.57) | $Al^{3+}$(0.57) | — | 0.52 | 2.2 | 16.1(2.5) | 13.3(1.3) |

TABLE 18-continued

| | Mol number (mmols/g) per g of polymerizable monomer | | | | | Durability of adhesion Adhesion test B/MPa (standard deviation) | |
|---|---|---|---|---|---|---|---|
| Ex. No. | Phosphoric acid-type monomer (A1) | Multivalent metal ion | Anion | $R_E$ | pH | Enamel | Dentin |
| 28 | PM1(1.38), PM2(0.56) | Al$^{3+}$(0.57) | — | 0.51 | 2.1 | 15.1(2.7) | 12.3(1.5) |
| 29 | PM1(1.37), PM2(0.57) | Al$^{3+}$(0.30), La$^{3+}$(0.11), Ca$^{2+}$(0.03) | F$^-$(0.75) | 0.37 | 1.7 | 18.4(1.8) | 16.2(2.4) |
| 30 | PM1(1.38), PM2(0.55) | Al$^{3+}$(0.85), La$^{3+}$(0.33), Ca$^{2+}$(0.09) | F$^-$(2.4) | 1.07 | 2.3 | 19.1(5.3) | 16.8(1.9) |
| 31 | PM1(1.38), PM2(0.55) | Al$^{3+}$(0.86), La$^{3+}$(0.32), Ca$^{2+}$(0.09) | F$^-$(2.3) | 1.07 | 2.3 | 20.1(2.3) | 16.5(1.2) |
| 32 | PM1(0.56), PM2(0.24) | Al$^{3+}$(0.86), La$^{3+}$(0.32), Ca$^{2+}$(0.09) | F$^-$(2.4) | 2.60 | 3.8 | 17.1(2.3) | 15.8(2.1) |
| 33 | PM1(1.39), PM2(0.56) | Al$^{3+}$(0.83), La$^{3+}$(0.33), Ca$^{2+}$(0.09) | F$^-$(2.4) | 1.04 | 2.2 | 18.1(5.4) | 14.1(3.1) |
| *9 | PM1(1.37), PM2(0.54) | Al$^{3+}$(0.57) | — | 0.52 | 2.2 | 12.1(4.1) | 8.7(4.1) |
| *10 | PM1(1.36), PM2(0.57) | Al$^{3+}$(0.86), La$^{3+}$(0.32), Ca$^{2+}$(0.09) | F$^-$(2.4) | 1.08 | 2.2 | 12.2(2.6) | 8.3(1.3) |
| *11 | PM1(1.36), PM2(0.57) | Al$^{3+}$(0.87), La$^{3+}$(0.33), Ca$^{2+}$(0.09) | F$^-$(2.5) | 1.09 | 2.2 | 12.3(3.5) | 9.3(1.5) |

*9 to 11 are Comparative Experiments.

As will be understood from the above experimental results, upon being blended with the fumed silica, the adhesive compositions of the invention used as the pretreating agents exhibit greatly improved adhesiveness to either the enamel or the dentin.

The invention claimed is:

1. An adhesive composition for dental use exhibiting acidic property, which includes a mixture of a polymerizable monomer component (A) containing an acid group containing polymerizable monomer, which has a group represented by >P(=O)OH as the acid group, a multivalent metal ion-releasing component (B), water (C) and fumed silica (D); wherein
said multivalent metal ion-releasing component (B) is capable of releasing at least earth metal ions;
earth metal ions stemming from said component (B) are present together with the acid group containing polymerizable monomer in such an amount that a total valency ratio ($R_E$) defined by the following formula (1) is in a range of 0.2 to 3.0 in said composition;

$$R_E = TV_E/TV_A \qquad (1)$$

wherein $TV_E$ is a total valency of the earth metal ions contained in said composition, and
$TV_A$ is a total valency of the acid groups of the acid group containing polymerizable monomer contained in said composition;
said polymerizable monomer component (A) contains not less than 5 mass % of the acid group containing polymerizable monomer,
said water (C) is contained in an amount of 3 to 150 mass parts per 100 mass parts of the polymerizable monomer component (A), and
said fumed silica (D) is contained in an amount of 0.5 to 20 mass parts per 100 mass parts of the polymerizable monomer component (A), wherein the composition comprises the components (A)-(D) contained in one package.

2. The adhesive composition for dental use according to claim 1, wherein said earth metal is aluminum and/or lanthanum.

3. The adhesive composition for dental use according to claim 1, wherein said component (B) is an earth metal ion-eluting filler.

4. The adhesive composition for dental use according to claim 1, wherein said component (B) is a carbonate of an acid and an earth metal, a lower alkoxide of an earth metal having not more than 4 carbon atoms.

5. The adhesive composition for dental use according to claim 1, wherein said acid group containing polymerizable monomer is a compound having a dihydrogenphosphoric monoester group and/or a hydrogenphosphoric diester group.

6. The adhesive composition for dental use according to claim 1, further containing a polymerization initiator (E).

7. A method of producing an adhesive composition for dental use comprising following steps of;
homogeneously mixing:
(A) a polymerizable monomer component containing not less than 5 mass % of an acid group containing polymerizable monomer which has a group represented by >P(=O)OH as the acid group;
(B) a multivalent metal ion-releasing component capable of releasing at least earth metal ions;
(C) water in an amount of 3 to 150 mass parts per 100 mass parts of the polymerizable monomer component (A); and
(D) fumed silica in an amount of 0.5 to 20 mass parts per 100 mass parts of the polymerizable monomer component (A); and
aging the obtained mixture so that the amount of the earth metal ions released from said component (B) into the obtained mixture maintains a total valency ratio ($R_E$) defined by the following formula (1) to lie in a range of 0.2 to 3.0;

$$R_E = TV_E/TV_A \qquad (1)$$

wherein $TV_E$ is a total valency of the earth metal ions contained in said mixture, and $TV_A$ is a total valency of the acid groups of the acid group containing polymerizable monomer contained in said mixture.

8. The method according to claim 7, wherein an earth metal ion-eluting filler is used as said multivalent metal ion-releasing component (B).

* * * * *